(12) United States Patent  
Sturm et al.

(10) Patent No.: US 9,221,771 B2  
(45) Date of Patent: Dec. 29, 2015

(54) METHOD FOR THE PREPARATION OF SUBSTITUTED OXAZOLIDINONES

(75) Inventors: Hubert Sturm, Kundl/Tirol (AT); Kerstin Knepper, Kundl/Tirol (AT)

(73) Assignee: Sandoz AG, Basel (CH)

( * ) Notice: Subject to any disclaimer, the term of this patent is extended or adjusted under 35 U.S.C. 154(b) by 171 days.

(21) Appl. No.: 14/111,365

(22) PCT Filed: Apr. 11, 2012

(86) PCT No.: PCT/EP2012/056551  
§ 371 (c)(1),  
(2), (4) Date: Jan. 30, 2014

(87) PCT Pub. No.: WO2012/140061  
PCT Pub. Date: Oct. 18, 2012

(65) Prior Publication Data  
US 2014/0213784 A1    Jul. 31, 2014

(30) Foreign Application Priority Data  
Apr. 11, 2011  (EP) .................................. 11161857

(51) Int. Cl.  
*C07D 265/30* (2006.01)  
*C07D 265/32* (2006.01)  
*C07D 413/10* (2006.01)  
*C07D 417/14* (2006.01)  
*C07D 487/18* (2006.01)

(52) U.S. Cl.  
CPC ............ *C07D 265/30* (2013.01); *C07D 265/32* (2013.01); *C07D 413/10* (2013.01); *C07D 417/14* (2013.01); *C07D 487/18* (2013.01)

(58) Field of Classification Search  
CPC .. C07D 265/30; C07D 265/32; C07D 413/10; C07D 417/14; C07D 487/18  
See application file for complete search history.

(56) References Cited

U.S. PATENT DOCUMENTS

| | | |
|---|---|---|
| 7,429,661 B2 | 9/2008 | Rao et al. |
| 7,598,378 B2 | 10/2009 | Thomas et al. |
| 7,741,480 B2 | 6/2010 | Rao et al. |
| 8,106,192 B2 | 1/2012 | Thomas |
| 8,435,989 B2 | 5/2013 | Bodhuri et al. |
| 2007/0066615 A1 | 3/2007 | Gerdes et al. |
| 2013/0316999 A1 | 11/2013 | Straub et al. |

FOREIGN PATENT DOCUMENTS

EP    0 515 272 A1    11/1992

*Primary Examiner* — Rebecca Anderson  
(74) *Attorney, Agent, or Firm* — IPLM Group, P.A.

(57) ABSTRACT

The present invention relates to methods for the preparation of a compound having the formula (X). Individual reaction steps as well as intermediates are additionally claimed.

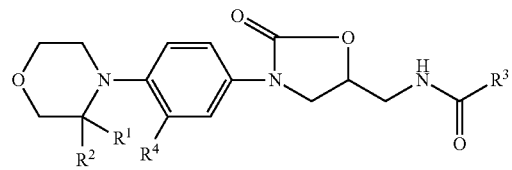

13 Claims, 6 Drawing Sheets

METHOD FOR THE PREPARATION OF SUBSTITUTED OXAZOLIDINONES

CROSS REFERENCE TO RELATED APPLICATIONS

This application is a national stage filing under 35 U.S.C. §371 of International Application No. PCT/EP2012/056551 filed Apr. 11, 2012, which claims priority under 35 U.S.C. §119 to European Application No. 11161857.5 filed Apr. 11, 2011.

FIELD OF THE INVENTION

The present invention relates to methods for the preparation of a compound having the formula (X). Individual reaction steps as well as intermediates are additionally claimed.

BACKGROUND OF THE INVENTION

The compound having the formula (X-1) has been disclosed in WO 01/47919.

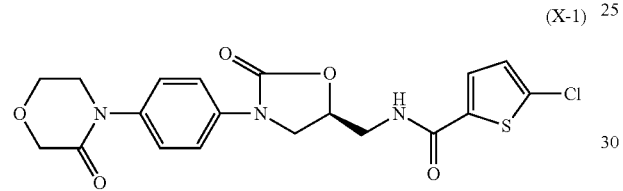
(X-1)

It is also known as rivaroxaban and is marketed in a number of countries under the trade designation Xarelto®.

The compound having the formula (X-1) acts as an inhibitor of clotting factor Xa and may be used as an agent for the prophylaxis and/or treatment of thromboembolic disorders, especially myocardial infarction, angina pectoris (including unstable angina), reocclusions and restenoses after angioplasty or aortocoronary bypass, stroke, transient ischemic attacks, peripheral arterial occlusive diseases, pulmonary embolisms or deep venous thromboses.

One method for preparing the compound having the formula (X-1) is disclosed in WO 2004/060887.

A further known compound has the formula (X-2)

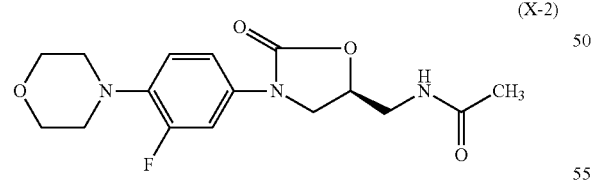
(X-2)

which is referred to as linezolid and is commerically available under the trade designation Zyvoxid®. It is useful as an antibiotic for treating infections caused by Gram-positive bacteria because it functions as a protein synthesis inhibitor.

EP-A-515 272 describes chiral sulfates and their use in the preparation of pharmaceuticals.

WO 01/047919 discloses substituted oxazolidinones and their use in the field of blood coagulation.

It was an object of the present invention to provide a simple and cost-effective method of preparing a compound having the formula (X). The present method is advantageous because it can use less expensive starting materials, such as (S)-3-chloro-1,2-propanediol. Furthermore, it has the option of performing several steps of the synthesis as a one-pot process which reduces the number of isolation steps. The synthesis of the compound having the formula (IV) can be performed as a one-pot reaction starting, e.g., from (S)-3-chloro-1,2-propanediol. Also the synthesis of the compound having the formula (VIII) can be performed as a one-pot reaction starting from the compound having the formula (IV).

SUMMARY OF THE INVENTION

The following compounds are referred to in the present invention:

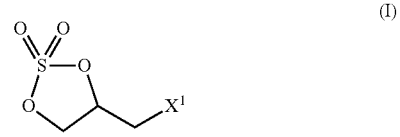
(I)

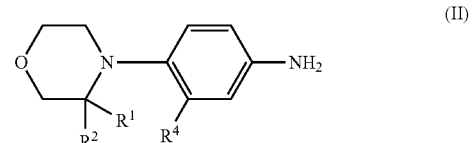
(II)

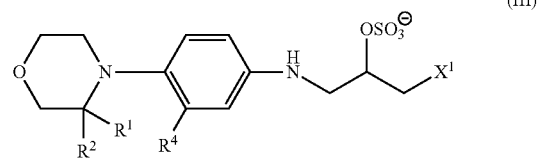
(III)

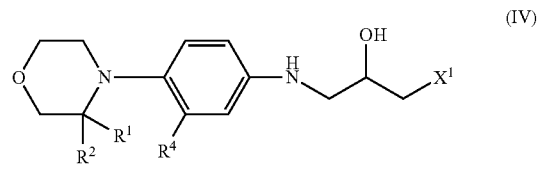
(IV)

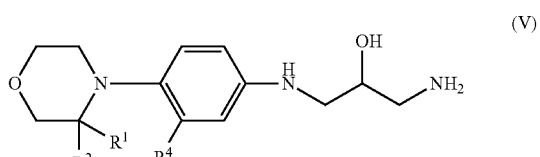
(V)

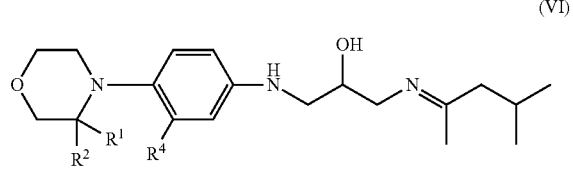
(VI)

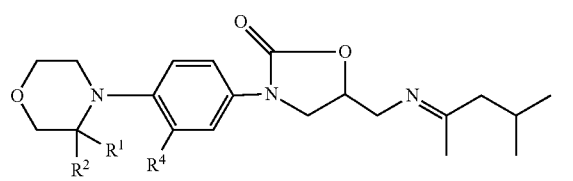
(VII)

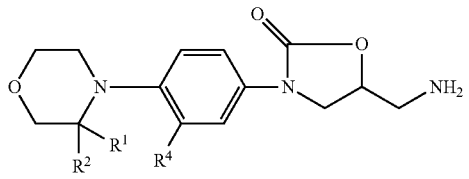
(VIII)

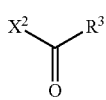
(IX)

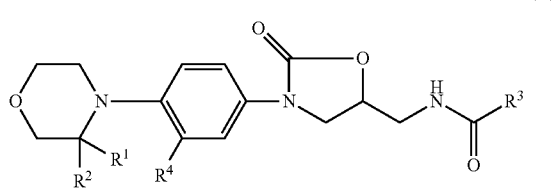
(X)

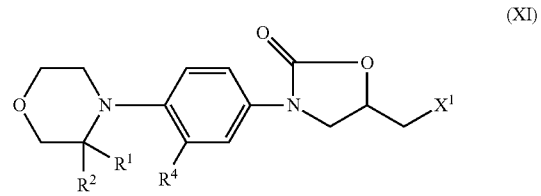
(XI)

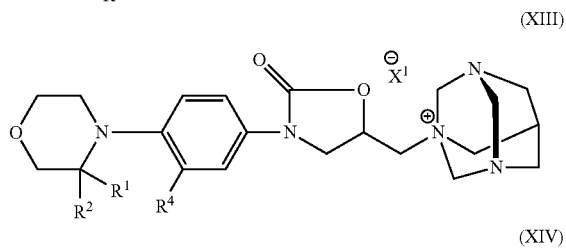
(XIII)

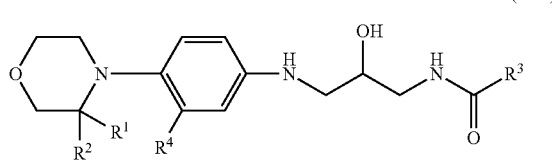
(XIV)

The following definitions apply throughout the application unless defined otherwise.

$X^1$ is a leaving group which is preferably selected from the group consisting of halogen such as F, Cl, Br or I. Preferably $X^1$ is a halogen, more preferably $X^1$ is Cl or I.

$X^2$ is a leaving group which is preferably selected from the group consisting of halogen such as F, Cl, Br or I. Preferably $X^2$ is a halogen, more preferably $X^2$ is Cl.

The moiety $C(R^1)(R^2)$ is either C=O or $CH_2$. In one preferred embodiment the moiety $C(R^1)(R^2)$ is C=O. In an alternative preferred embodiment, the moiety $C(R^1)(R^2)$ is $CH_2$.

$R^3$ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S. The alkyl group can be optionally substituted, e.g., by one or more (e.g., 1 to 3) substituents which are independently selected from the group consisting of halogen (such as F, Cl, Br, I), hydroxy, $C_{1-4}$ alkoxy, CN, and isocyanate (OCN). The aryl group and the heterocyclic group can be optionally substituted, e.g., by one or more (e.g., 1 to 3) substituents which are independently selected from the group consisting of $C_{1-6}$ alkyl, halogen (such as F, Cl, Br, I), hydroxy, $C_{1-4}$ alkoxy, CN, and OCN. In one preferred embodiment $R^3$ is preferably an optionally substituted heterocyclic group, more preferably

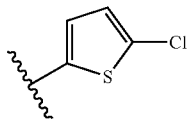 [SMILES: *c1ccc(Cl)s1]

In a second preferred embodiment, $R^3$ is preferably $C_{1-6}$ alkyl, more preferably methyl.

$R^4$ is H or halogen (such as F, Cl, Br or I). In one preferred embodiment $R^4$ is H. In an alternative preferred embodiment, $R^4$ is halogen, in particular Cl or F, more particularly F.

All of the above compounds can be provided in racemic or enantiomerically enriched or pure form. The compound having the formula (I) can be a racemic mixture or an optically enriched or pure enantiomer. The optical purity of the compound having the formula (I) directly influences the optical purity of the produced compounds having the fomulae (III), (IV), (V), (VI), (VII), (VIII) (X), (XI), (XII) and (XIV). Compounds having a high optical purity result in products having a high optical purity. Starting synthesis with the pure S-isomer of the compound having the formula (I) by the designated routes A, B and C produces the compounds having the formulae (X-1) and (X-2) with high optical purity. If a racemic mixture of the compound having the formula (I) is used as a starting material, racemic products are obtained that can be separated by usual methods like crystallization and chromatography. The preferred starting material (compound of formula (I)) is the S-isomer of the compound of formula (I).

In a preferred embodiment the compounds are provided in enantiomeric form, e.g., having an e.e. of at least about 99, preferably at least about 99.9. In one preferred embodiment, the compounds are provided in an enantiomeric form, so that the preparation method results in the following compound (X):

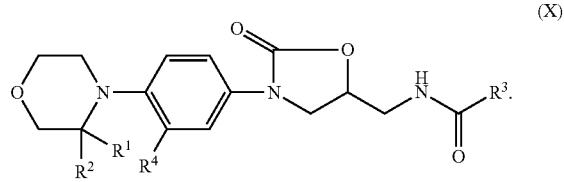
(X)

In one preferred embodiment, $CR^1R^2$ is C=O, $R^4$ is H and $R^3$ is a substituted heterocyclic group having the formula

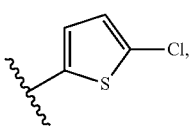

i.e. the compound having the formula (X) has the formula (X-1). In an alternative embodiment $CR^1R^2$ is $CH_2$, $R^4$ is F and $R^3$ is $CH_3$, i.e. the compound having the formula (X) has the formula (X-2).

In one embodiment, the invention provides a method comprising the steps of:

Step i: reacting a compound having the formula (I) with a compound having the formula (II) to provide a compound having the formula (III)

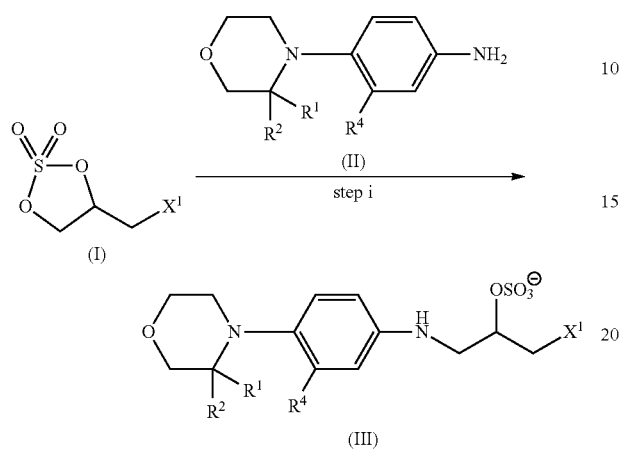

Step ii: converting the sulfate moiety of the compound having the formula (III) into a hydroxy group in the presence of water to provide a compound having the formula (IV)

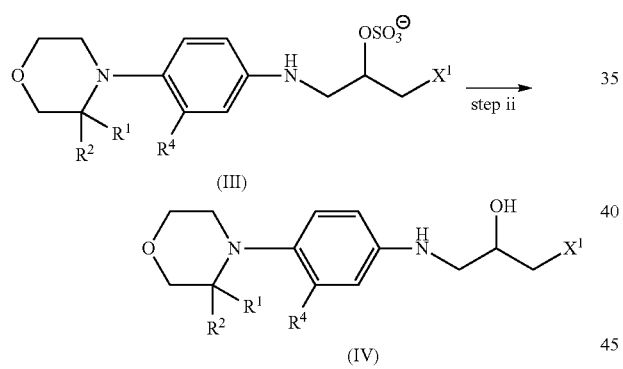

Step iii: replacing the leaving group $X^1$ of the compound having the formula (IV) by $NH_3$ to provide a compound having the formula (V)

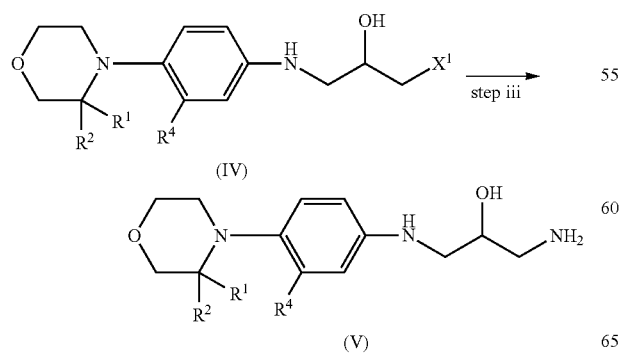

Step iv: reacting the compound having the formula (V) with methylisobutylketone to provide a compound having the formula (VI)

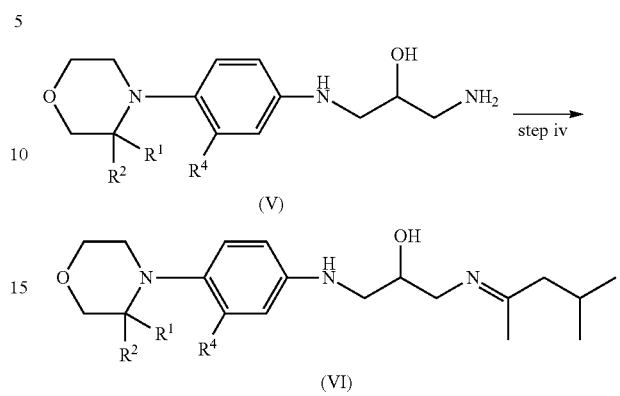

Step v: cyclizing the compound having the formula (VI) to provide a compound having the formula (VII)

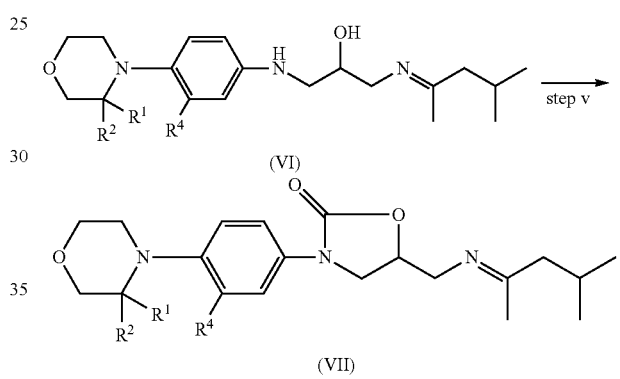

Step vi: removing the methylisobutylketone group from the compound having the formula (VII) to provide a compound having the formula (VIII)

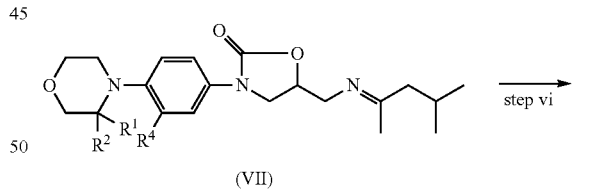

Step vii: reacting the compound having the formula (VIII) with a compound having the formula (IX) to provide a compound having the formula (X)

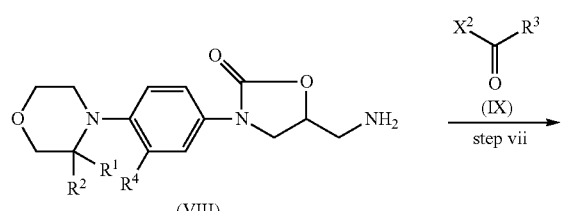

(VIII)

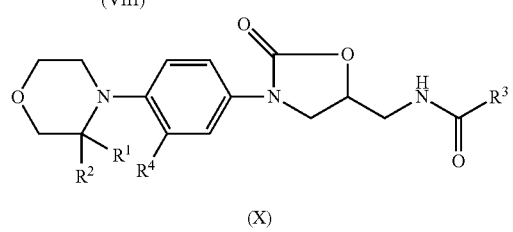

(X)

wherein

X¹ is a leaving group;

X² is a leaving group which can be the same or different than X¹;

the moiety $C(R^1)(R^2)$ is C=O or $CH_2$;

R³ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S, wherein the alkyl group, the aryl group and the heterocyclic group can be optionally substituted; and R⁴ is H or halogen.

A further embodiment of the present invention is a method comprising the steps of:

Step i: reacting a compound having the formula (I) with a compound having the formula (II) to provide a compound having the formula (III)

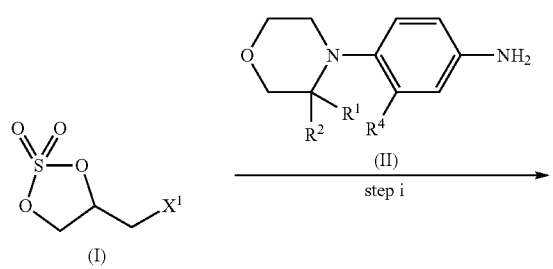

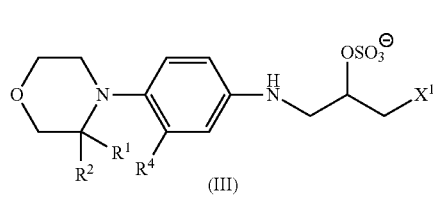

Step ii: converting the sulfate moiety of the compound having the formula (III) into a hydroxy group in the presence of water to provide a compound having the formula (IV)

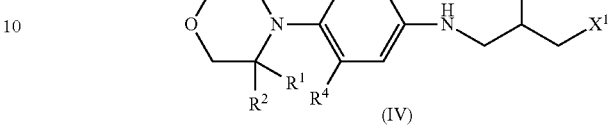

Step viii: cyclizing the compound having the formula (IV) to provide a compound having the formula (XI)

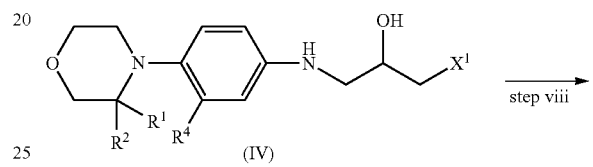

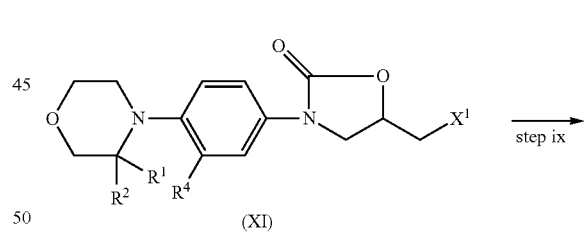

Step ix: optionally replacing the leaving group X¹ in the compound (XI) by a different leaving group X¹ to provide a compound having the formula (XII)

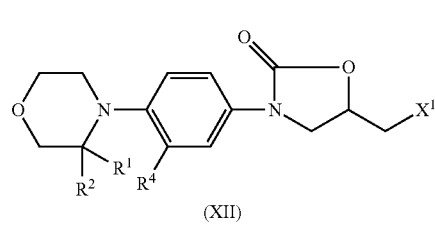

Step x: reacting the compound having the formula (XI) or (XII) with hexamethylenetetramine to provide a compound having the formula (XIII)

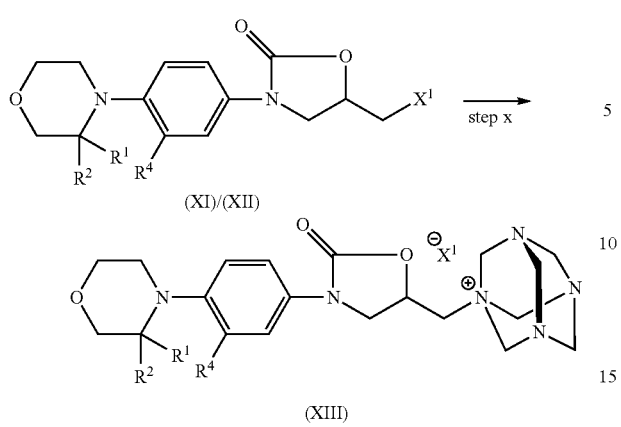

(XI)/(XII)

(XIII)

Step xi: removing the hexamethylenetetramine moiety of the compound having the formula (XIII) to provide a compound having the formula (VIII)

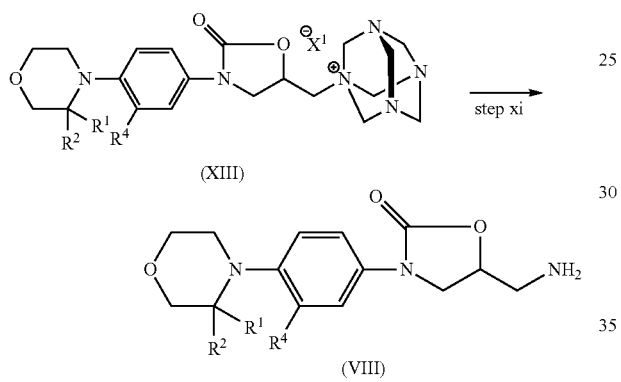

(XIII)

(VIII)

Step vii: reacting the compound having the formula (VIII) with a compound having the formula (IX) to provide a compound having the formula (X)

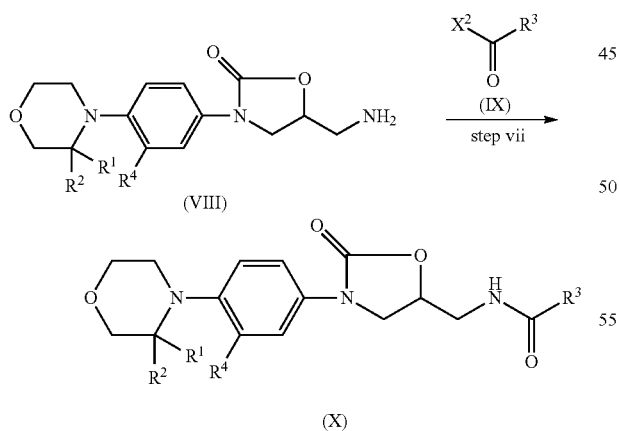

(VIII)

(X)

wherein
$X^1$ is a leaving group;
$X^2$ is a leaving group which can be the same or different than $X^1$;
the moiety $C(R^1)(R^2)$ is C=O or $CH_2$;
$R^3$ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S, wherein the alkyl group, the aryl group and the heterocyclic group can be optionally substituted; and $R^4$ is H or halogen.

In yet another embodiment, the present invention provides a method comprising the steps of:

Step i: reacting a compound having the formula (I) with a compound having the formula (II) to provide a compound having the formula (III)

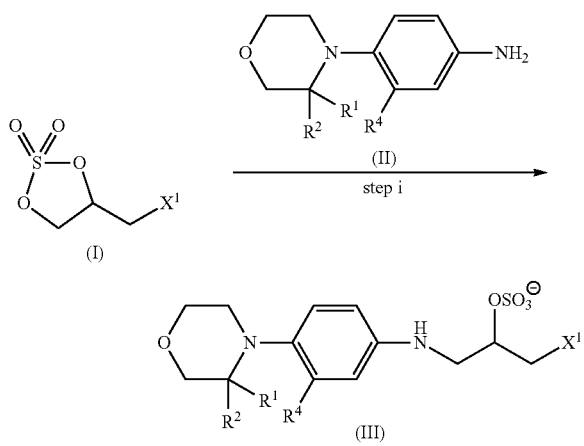

(I)

(II)

(III)

Step ii: converting the sulfate moiety of the compound having the formula (III) into a hydroxy group in the presence of water to provide a compound having the formula (IV)

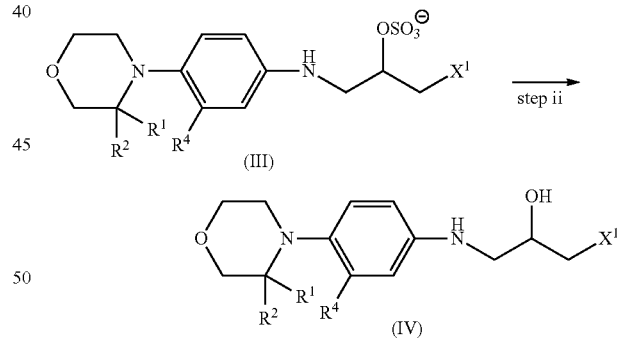

(III)

(IV)

Step iii: replacing the leaving group $X^1$ of the compound having the formula (IV) by $NH_3$ to provide a compound having the formula (V)

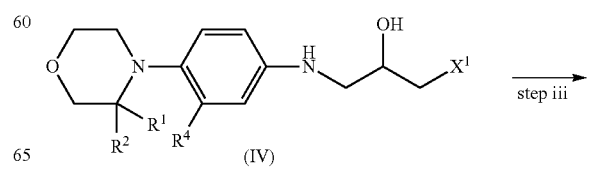

(IV)

-continued

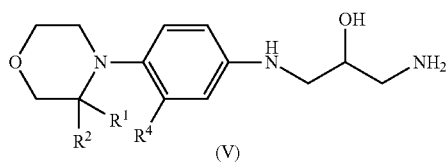

Step xii: reacting the compound having the formula (V) with a compound having the formula (IX) to provide a compound having the formula (XIV)

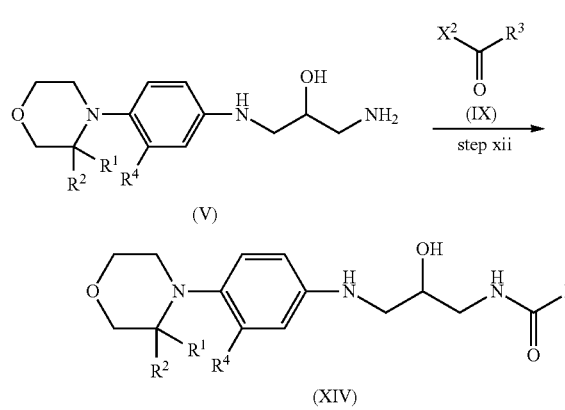

Step xiii: cyclizing the compound having the formula (XIV) to provide a compound having the formula (X)

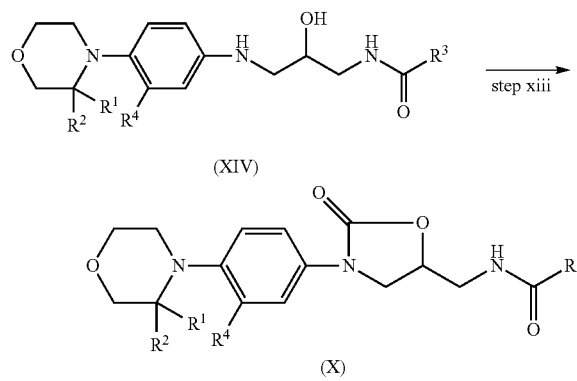

wherein
X$^1$ is a leaving group;
X$^2$ is a leaving group which can be the same or different than X$^1$;
the moiety C(R$^1$)(R$^2$) is C=O or CH$_2$;
R$^3$ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S, wherein the alkyl group, the aryl group and the heterocyclic group can be optionally substituted; and
R$^4$ is H or halogen.

A method comprising the step of

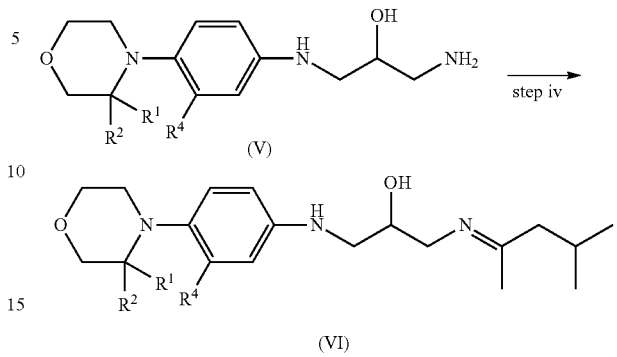

wherein R$^1$, R$^2$, and R$^4$ are as defined above, is also disclosed.

The present invention furthermore provides a method comprising the step of:

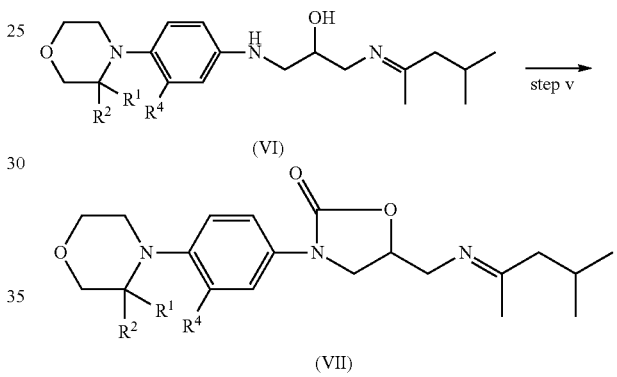

wherein R$^1$, R$^2$, and R$^4$ are as defined above.

A further embodiment of the present invention refers to a method comprising the step of:

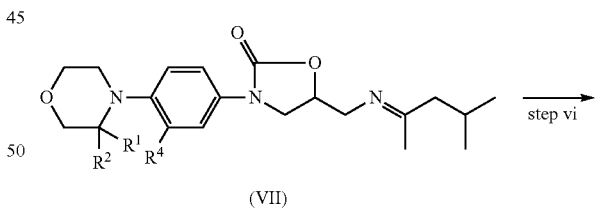

wherein R$^1$, R$^2$, and R$^4$ are as defined above.

Another embodiment of the present invention provides a method comprising the step of:

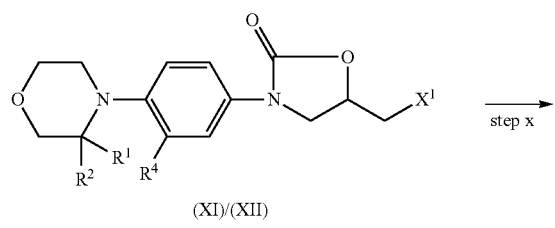

(XI)/(XII)

step x

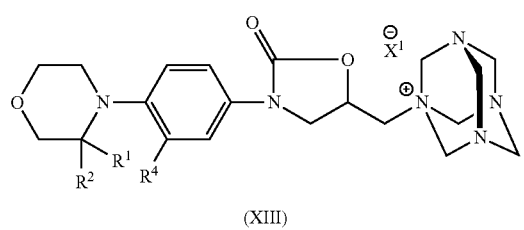

(XIII)

wherein $X^1$, $R^1$, $R^2$, and $R^4$ are as defined above.

In another embodiment, the present invention relates to a method comprising the step of:

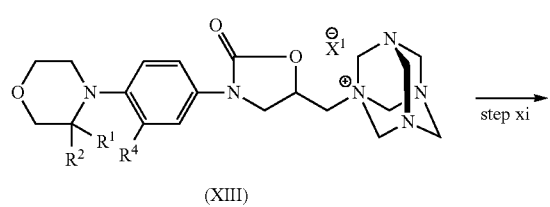

(XIII)

step xi

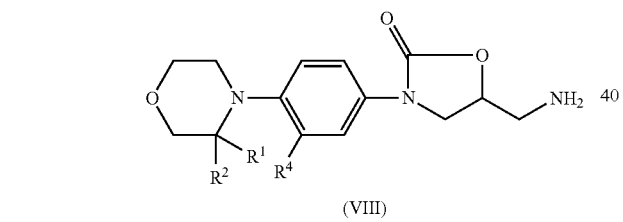

(VIII)

wherein $X^1$, $R^1$, $R^2$, and $R^4$ are as defined above.

Preferred compounds are selected from the group consisting of:

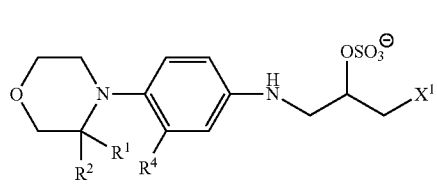

(III)

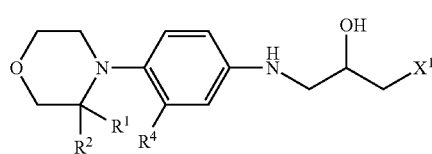

(IV)

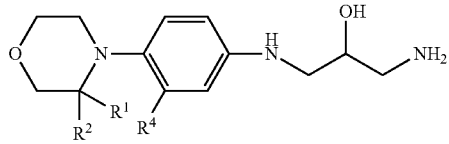

(V)

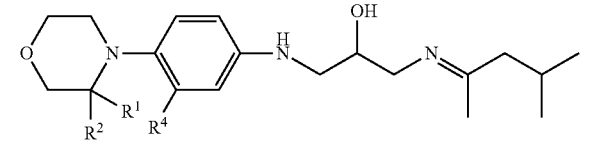

(VI)

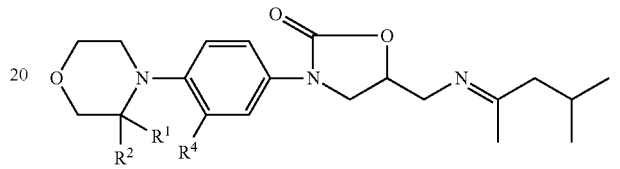

(VII)

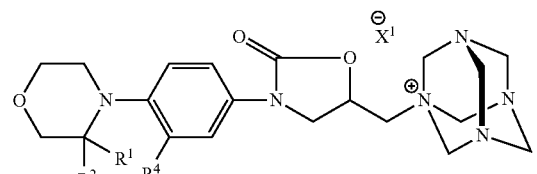

(XIII)

and are preferably selected from the group consisting of:

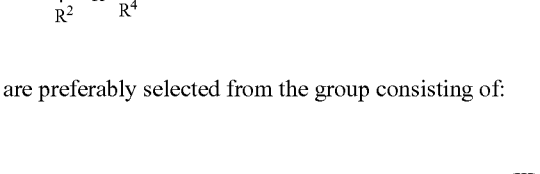

(III)

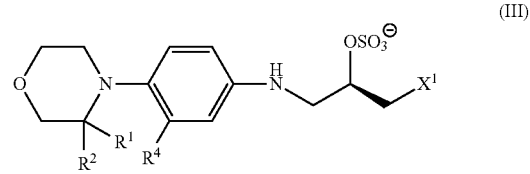

(IV)

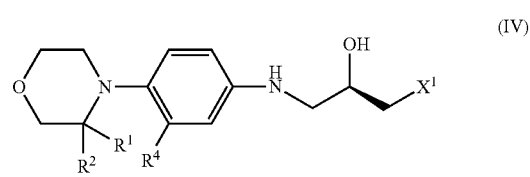

(V)

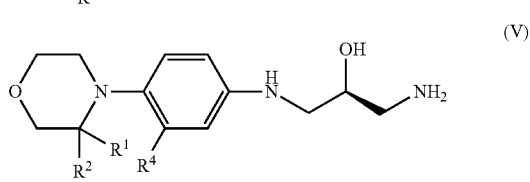

(VI)

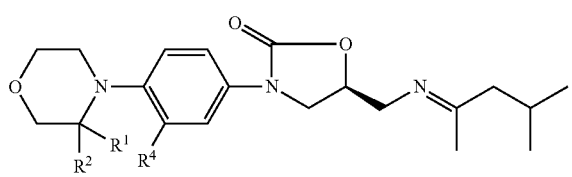

(VII)

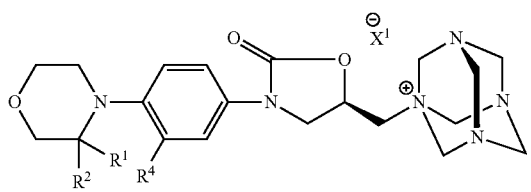

(XIII)

wherein $X^1$, $R^1$, $R^2$, and $R^4$ are as defined above.

DETAILED DESCRIPTION OF THE INVENTION

Figure 1:
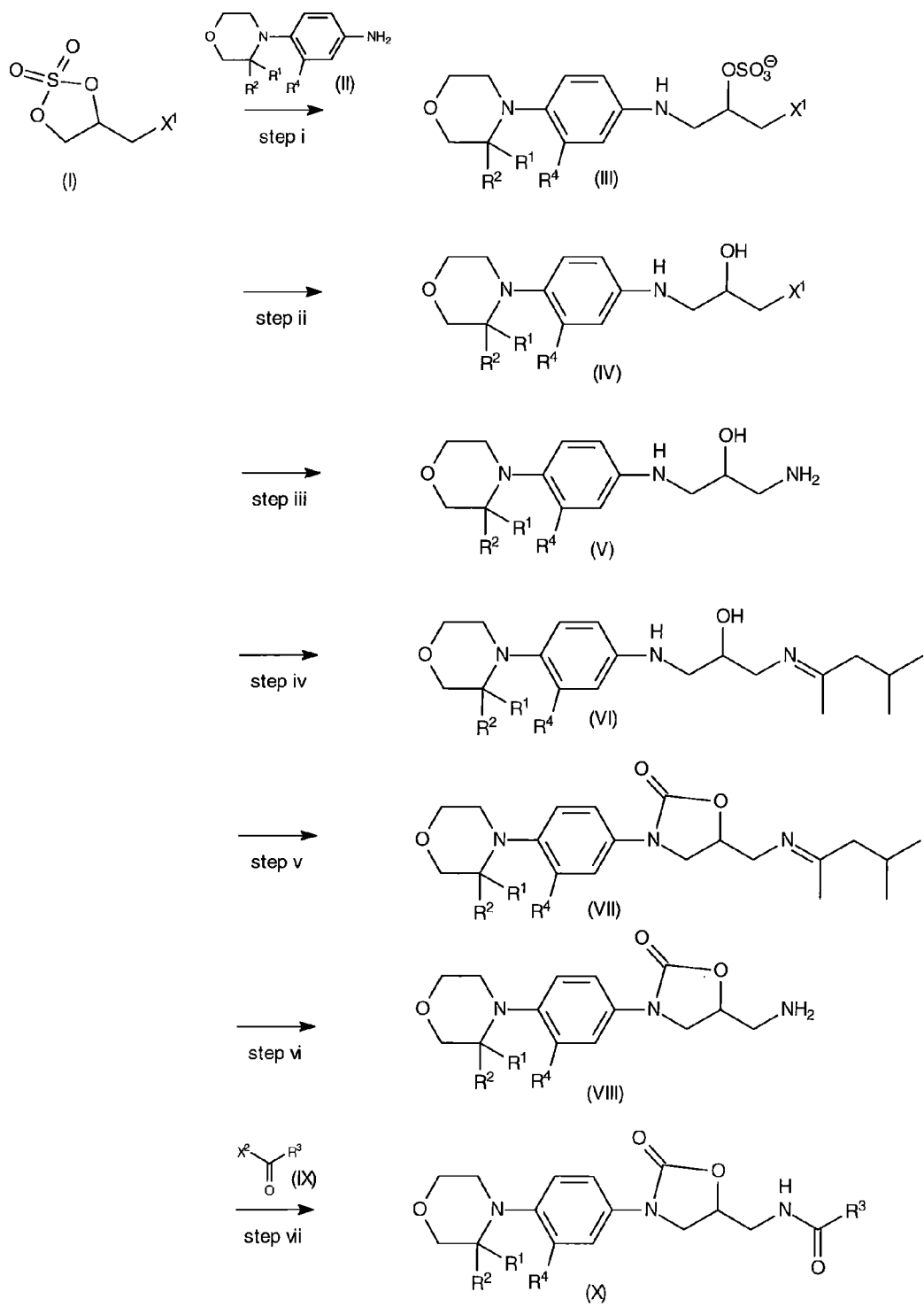
FIG. 1 summarizes a first reaction scheme according to the invention (route A).
Figure 2:
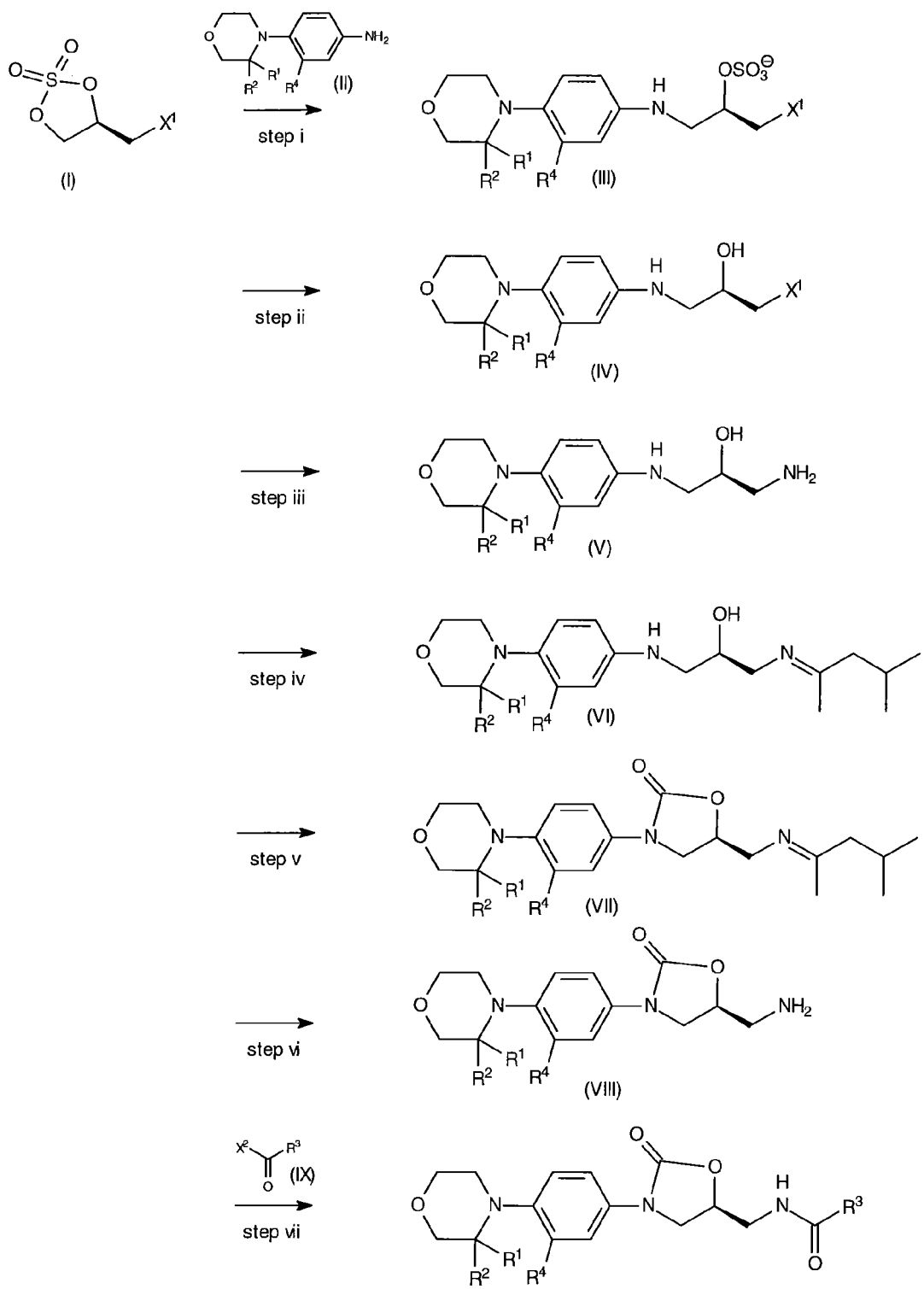
FIG. 2 summarizes a preferred embodiment of route A.
Figure 3:
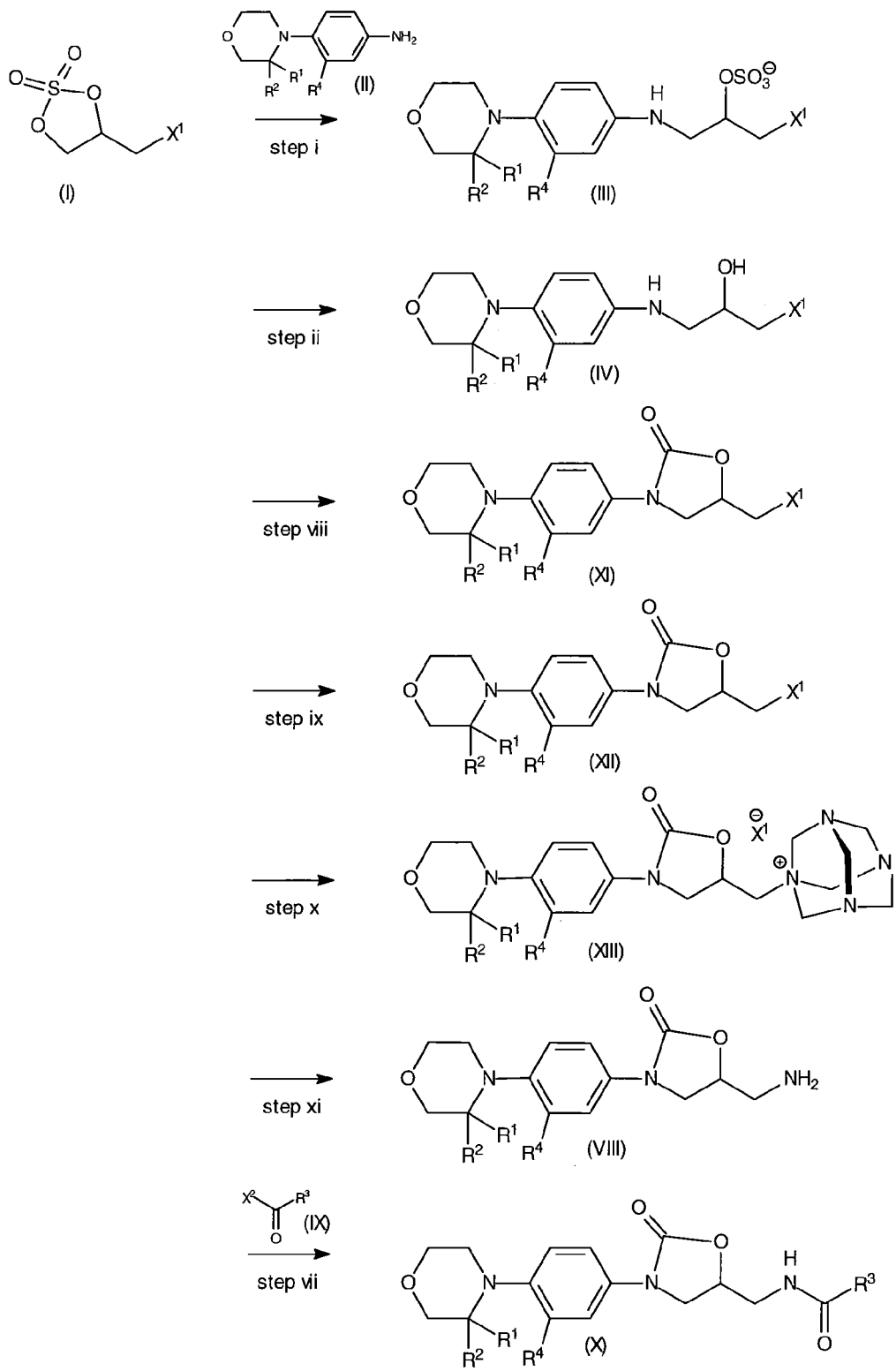
FIG. 3 summarizes a second reaction scheme according to the invention (route B).
Figure 4:
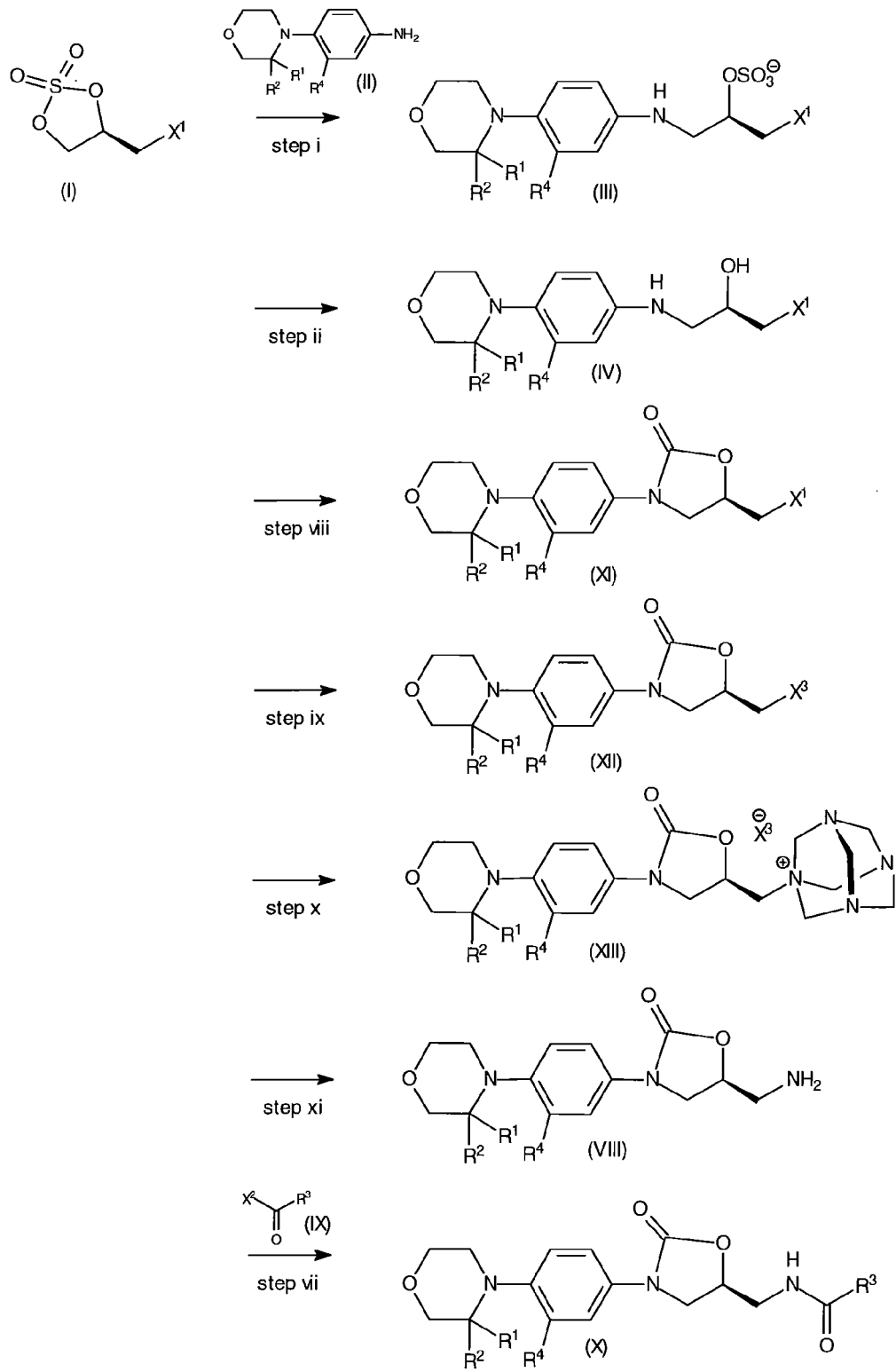
FIG. 4 summarizes a preferred embodiment of route B.
Figure 5:
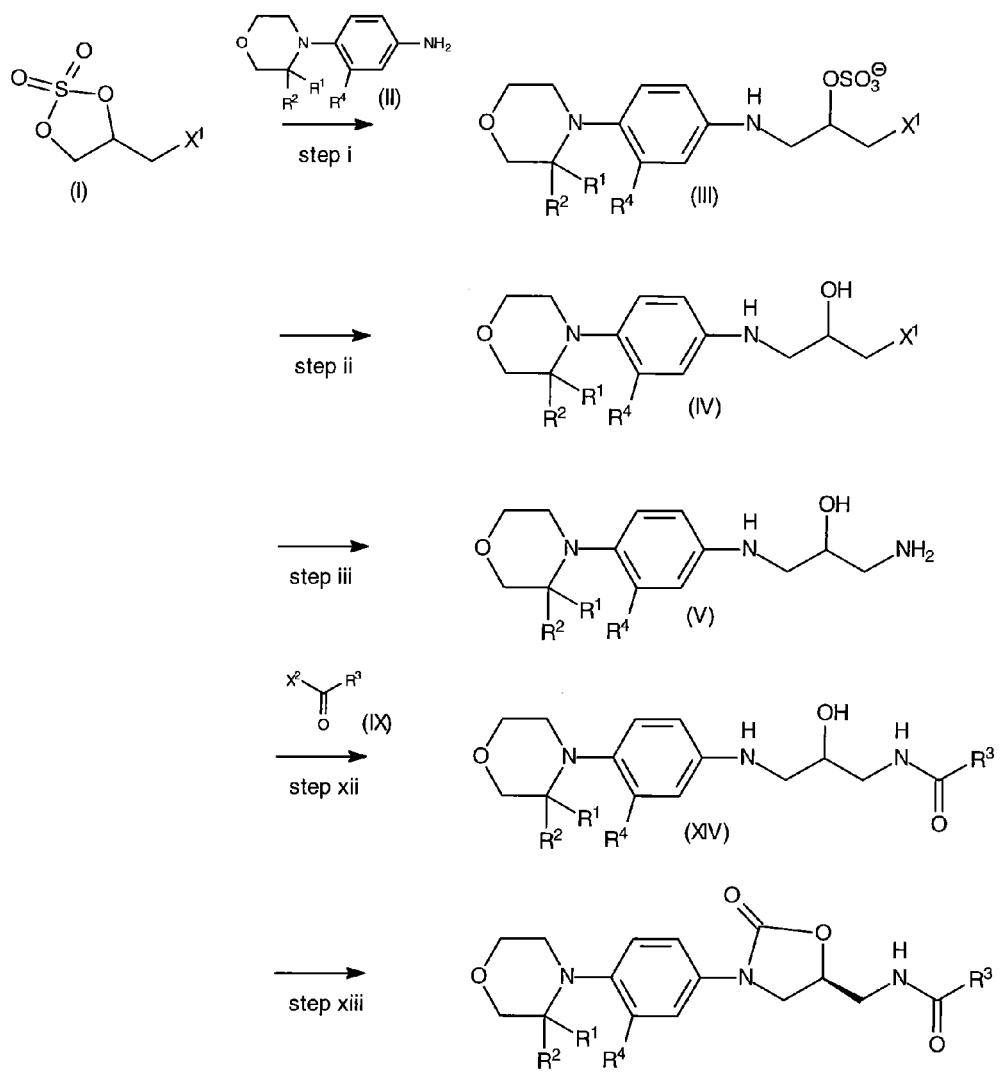
FIG. 5 summarizes a third reaction scheme according to the invention (route C).
Figure 6:
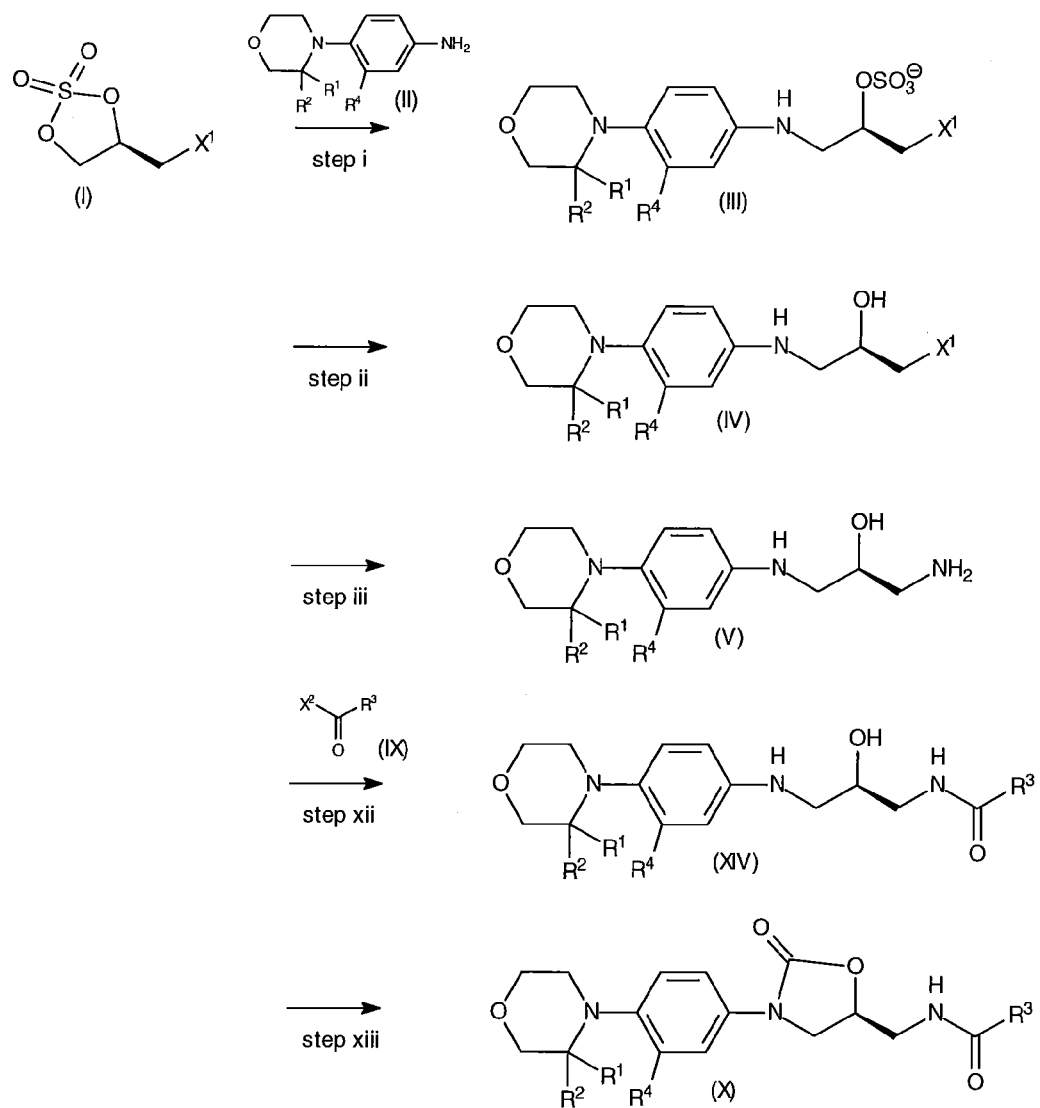
FIG. 6 summarizes a preferred embodiment of route C.

The compound having the formula (X) can be prepared by three interrelated routes, which are designated as routes A, B and C. The steps of the various routes will be explained in the following. It is understood that any of the reaction steps shown below can be claimed individually or in combination with one or more of the other steps.

Step i

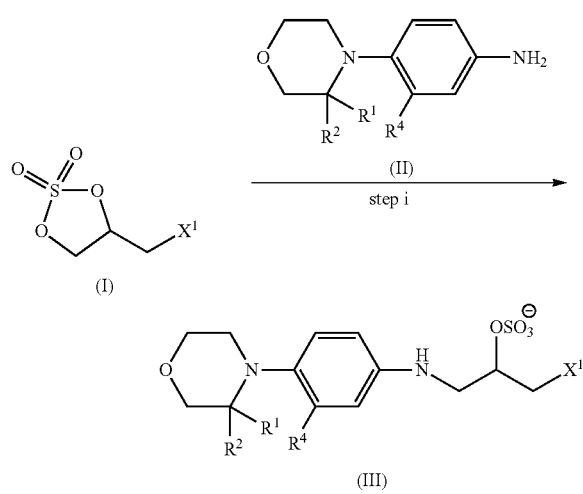

In step i, the compound having the formula (III) is prepared by reacting a compound having the formula (I) with a compound having the formula (II). The compound having the formula (I) can be prepared according to any known method such as that disclosed in example 1 of EP-A-515 272.

The compound having the formula (II) is commerically available from VUOS (CZ) or can be prepared according to known methods (cf., e.g., WO 2005/026135).

The molar ratio of the compound having the formula (I) and the compound having the formula (II) is preferably in the range of about 2 to about 1, more preferably about 1.4 to about 1.

The solvent used in the reaction step is typically a polar aprotic solvent, which can be, e.g., selected from nitrile solvents (such as acetonitrile), halogenated organic solvents (such as methylene chloride), esters such as (ethyl acetate), ethers (such as THF) as well as mixtures thereof. The solvent is preferably a nitrile solvent such as acetonitrile or a halogenated organic solvent such as methylene chloride.

The reaction can be conducted at any suitable temperature. Typical reaction temperatures range from about −20° C. to about 80° C., preferably from about 0° C. to about 40° C. More preferably the reaction is conducted at about room temperature (e.g., about 20° C. to about 25° C.).

The duration of the reaction will depend on the other reaction conditions chosen and can range from about 1 h to about 48 h, more typically from about 10 h to about 24 h.

The pH value is not critical, but best results will be achieved if pH >7 is used.

The cation of the compound having the formula (III) is not specifically restricted and will depend on the compounds and solvent used. It can, for example, be triethylammonium.

In order to achieve quantitative conversion of the compound having the formula (II) it is preferable to use of at least 1 equivalent of an organic or inorganic base. The preferred organic bases are trialkylamines (e.g., those having a $C_{1-6}$ alkyl group, such as triethylamine, ethyldiisopropylamine and tributylamine). The preferred inorganic bases include alkali carbonates (such as sodium and potassium carbonate) and alkali hydrogen carbonates (such as potassium and sodium hydrogen carbonate).

After the reaction has been completed, the compound having the formula (III) can be isolated from the reaction mixture and/or be purified or be used in the subsequent reaction without being isolated or purified. One method of isolating the compound having the formula (III) is filtration.

Step ii

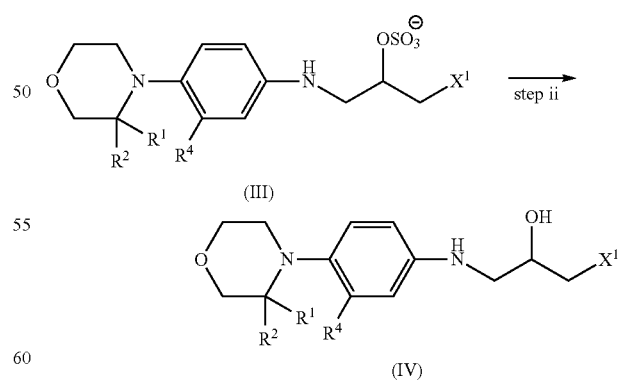

The sulfate moiety of the compound having the formula (III) is converted into a hydroxy group in the presence of water in step ii. This reaction can be conducted under any suitable conditions. Typically, the conversion will be conducted by acidic hydrolysis.

In one embodiment, the compound having the formula (III) will be contacted with an acid, e.g., selected from the group consisting of alkyl sulfonic acids (e.g., those having a $C_{1-6}$ alkyl group, such as methane sulfonic acid), aryl sulfonic acids (such as toluene sulfonic acid). The acid will be typically employed in a molar excess.

Step ii can be conducted in a polar organic solvent. Examples of typical solvents include nitrile solvents (such as acetonitrile), ethers (such as THF and dioxane), halogenated organic solvents (such as methylene chloride) and mixtures thereof.

The reaction temperature of step ii will be usually in the range of about −20° C. to about 80° C., preferably about 0° C. to about 40° C. Typically, the reaction will be conducted at about room temperature.

The duration of the reaction is not particularly limited. It will be typically completed within about 1 h to about 24 h, more typically about 2 h to about 12 h.

If desired, the compound (IV) can be isolated and/or purified before it is submitted to a subsequent reaction. However, this is not necessary, as it can also be reacted further without isolation or purification.

Step iii

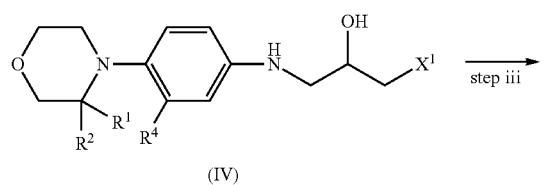

(IV)

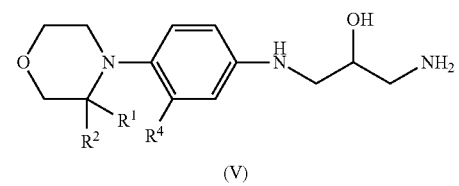

(V)

The leaving group $X^1$ of compound (IV) is replaced by $NH_3$ in step iii. The replacement can be conducted under any suitable conditions. According to one option, the compound having the formula (IV) can be contacted with aqueous ammonia. The ammonia is preferably employed in a molar excess, e.g., in an excess of at least about 40, preferably at least about 200. Although there is no particular limitation the concentration of the aqueous ammonia is preferably at least about 20%, more preferably at least about 25%.

The reaction temperature is not particularly limited and can be chosen appropriately. It is usually in the range of about 1 h to about 10 h, more usually about 2 h to about 5 h.

The reaction temperature is not restricted and can, e.g., be in the range of about −20° C. to about 40° C., such as in the range of about 0° C. to about 30° C. Step iii can, for example, be conducted at room temperature.

While it is possible to isolate and purify the compound having the formula (V), this is not necessary as it can be reacted further without isolation and/or purification.

Step iv

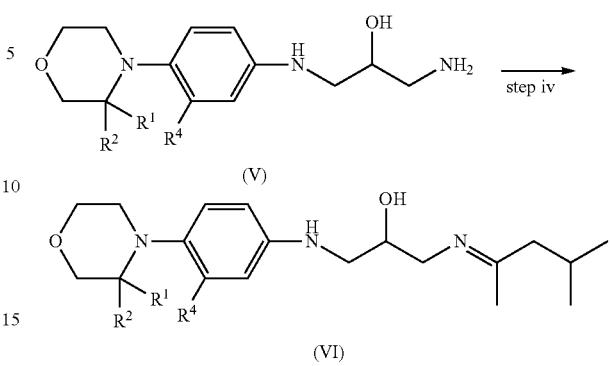

In step iv, the compound having the formula (V) is reacted with methylisobutylketone to provide a compound having the formula (VI). A skilled person will be able to chose suitable reaction conditions. It was surprisingly found that methylisobutylketone gave superior results compared to methylethylketone, diisopropylketone, methylamylketone and diisobutylketone. For example, the reaction yield using diisopropylketone was only 20%.

In one embodiment, the reaction can be conducted under basic conditions. For example, a base such as an alkali or alkaline earth carbonate, alkali or alkaline earth hydroxide or alkaline earth oxide can be added to the reaction mixture.

The reaction will be typically conducted at elevated temperature such as reflux temperature in order to facilitate the removal of water which is formed as a by-product. If other methods of removing water are used, the reaction conditions can be modified accordingly.

The reaction time can be chosen by a person skilled in the art. Typical reaction times are, for example, about 1 h to about 24 h, more typically about 3 h to about 5 h.

As a rule, no purification and/or isolation are required. However, the compound having the formula (VI) can be isolated and/or purified, if desired.

Step v

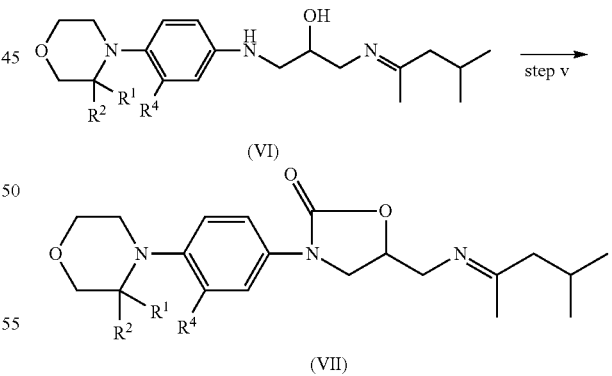

In step v, the compound having the formula (VI) is cyclized to provide a compound having the formula (VII). Any suitable cyclization reaction can be employed. In one embodiment, the cyclization is conducted using a cyclization agent selected from the group consisting of carbonyldiimidazol (such as N,N'-carbonyldiimidazol).

The cyclization agent is typically employed in an amount of about 1.2 mol to about 1.0 mol per 1 mol of the compound having the formula (VI).

Any suitable solvent can be used in step v. Typical solvents include nitriles (such as acetonitrile), aromatic hydrocarbons (such as toluene), and esters (such as butyl acetate). If the reaction of step v is conducted after the reaction of step iv, then the ketone which was used as a reactant in step iv will advantageously be used as a solvent in step v to avoid unnecessary isolation and purification steps.

The reaction can be conducted at any suitable temperature. Preferably the reaction temperature is in the range of about −20° C. to about 120° C., more preferably about 0° C. to about 50° C., e.g., at about room temperature.

The duration of the reaction will depend, e.g., on the other conditions chosen. It can vary, for example, in the range of about 1 h to about 24 h, more typically about 4 h to about 16 h.

The compound having the formula (VII) can be isolated and/or purified, if desired. However, this is not necessary for the subsequent reaction steps.

Step vi

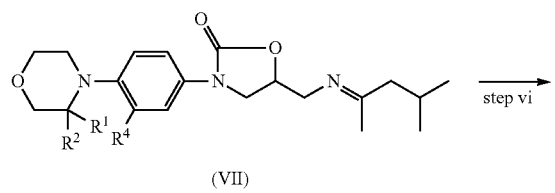

(VII)

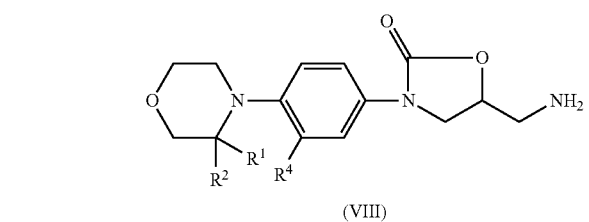

(VIII)

The methylisobutylketone group is removed from the compound having the formula (VII) in step vi to provide a compound having the formula (VIII). The conditions of this step are not particularly limited and treatment with an acid, such as an aqueous acid, can be employed. Typical acids include inorganic acids and organic acids. Examples of suitable inorganic acids include hydrochloric acid, sulfuric acid and phosphoric acid. Methane sulfonic acid, toluene sulfonic acid and oxalic acid are suitable as organic acids.

The cleavage can be conducted, for instance, at a temperature in the range of about 0.5° C. to about 3° C., such as about 1° C. to about 2° C. For example, approximately room temperature is suitable.

The duration of the reaction can be chosen accordingly by a skilled person. Suitable reaction times include about 0.25 h to about 10 h, and are preferably about 1 h.

Purification and/or isolation of the compound having the formula (VIII) is not required but can be conducted, if desired.

Step vii

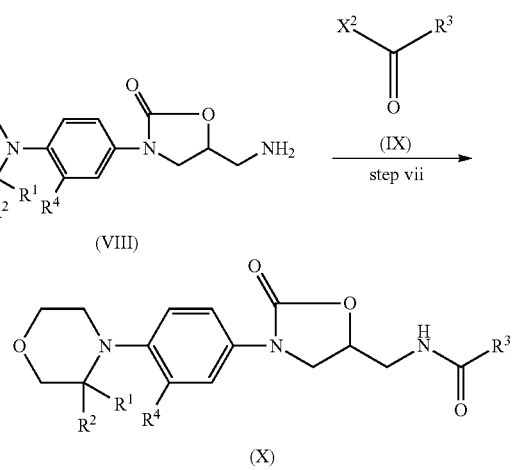

The compound having the formula (VIII) is reacted with a compound having the formula (IX) to provide a compound having the formula (X) in step vii.

The reaction can be conducted in an organic solvent such as a nitrile solvent (such as acetonitrile), an ether solvent (such as THF), an ester solvent (such as ethyl acetate), an amide solvent (such as DMF), a ketone solvent (such as acetone) or a halogenated hydrocarbon solvent (such as methylene chloride).

The reaction temperature is not particularly limited and can be, for example, in the range of about −20° C. to about 40° C., preferably about −10° C. to about 20° C.

Typical reaction times include about 0.5 h to about 3 h, more typically about 1 h to about 2 h.

If desired, organic or inorganic bases can be added to the reaction mixture. Examples of suitable organic bases include tri($C_{1-6}$ alkyl)amines, pyridine, and collidine. Suitable inorganic bases include alkali carbonates such as sodium or potassium carbonate.

The desired final product, the compound having the formula (X), can be isolated from the reaction mixture and/or be purified according to known methods.

Step viii

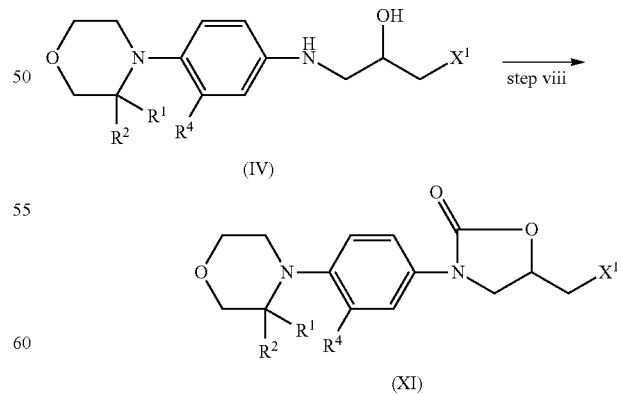

In step viii, the compound having the formula (IV) is cyclized to render a compound having the formula (XI). The same reaction conditions as discussed above with respect to step v apply for this reaction.

The compound having the formula (XI) can be isolated and/or purified or can be used as such in a subsequent reaction.

Step ix

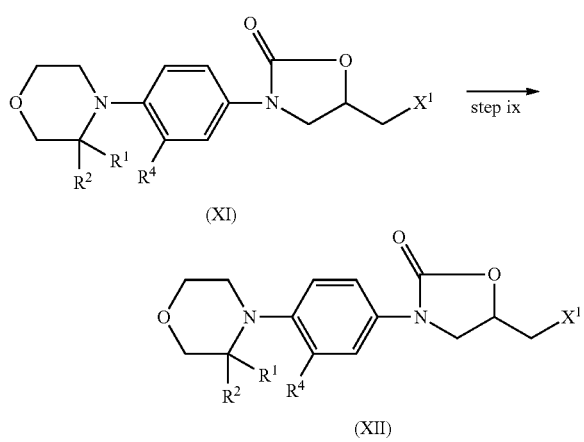

Step ix is an optional reaction step. In some cases it may be desirable to replace the leaving group $X^1$ by a different leaving group $X^1$ to adapt the reactivity for a subsequent reaction step. In one embodiment of the invention, for example, $X^1$=Cl can be replaced by $X^1$=I.

Step x

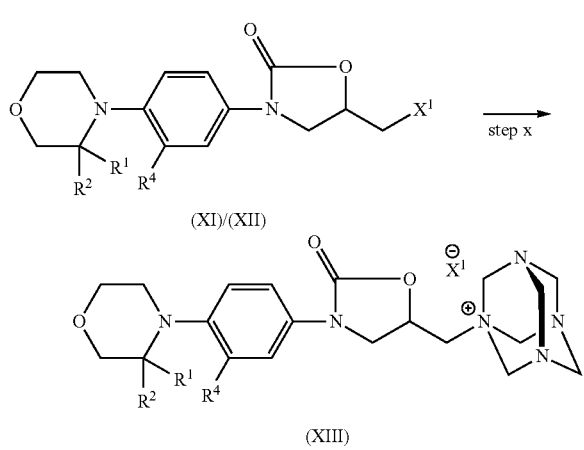

In this reaction step, the compound having the formula (XI) or (XII) is reacted with hexamethylenetetramine to provide a compound having the formula (XIII).

The reaction conditions are not particularly limited and can be chosen appropriately by a skilled person. For example, the reaction temperature can be from about 20° C. to about 100° C., preferably about 50° C. to about 70° C.

The reaction time can, e.g., be in the range of about 1 h to about 96 h, such as about 20 h to about 80 h.

Typical solvents which can be used in this reaction include sulfolane, N-methylpyrrolidone (NMP), dimethylformamide (DMF), dimethylsulfoxide (DMSO), tetramethylurethane (TMU) or mixtures thereof, with sulfolane being preferred.

The reaction can be conducted under an inert atmosphere such as a nitrogen atmosphere.

No purification and/or isolation of the product are required. However, they can be conducted, if desired.

Step xi

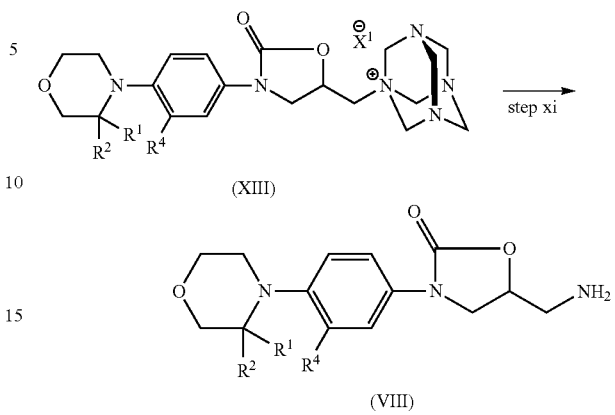

The hexamethylenetetramine moiety of the compound having the formula (XIII) is removed in order to provide a compound having the formula (VIII).

The hexamethylenetetramine moiety can be removed by any suitable method. In one embodiment, the hexamethylenetetramine moiety is removed by acid treatment. In this embodiment, the compound having the formula (XIII) is contacted with an acid in the presence of water. Typical acids include inorganic acids and organic acids. Examples of suitable inorganic acids include hydrochloric acid.

Typical reaction temperatures include about 0° C. to about 80° C., preferably about 40° C. to about 60° C.

The reaction will be typically completed within about 1 h to about 3 h but the exact duration will, of course, depend on the reaction conditions and can be chosen by a skilled person.

An inert atmosphere such as a nitrogen atmosphere can be used, if desired.

Purification and/or isolation of the product are not necessary but can be conducted, if desired.

Step xii

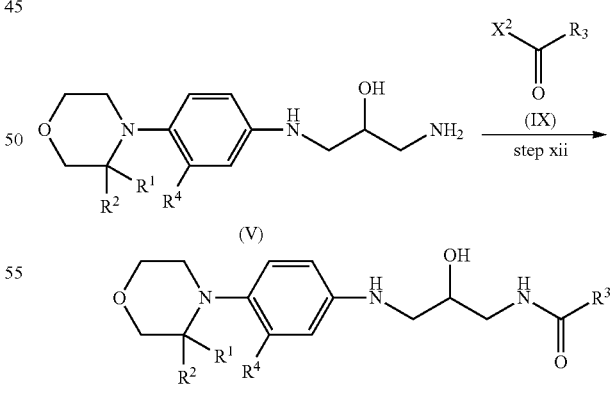

The compound having the formula (V) is reacted with the compound having the formula (IX) to provide a compound having the formula (XIV) in step xii. The conditions for this reaction step are analogous to those described above with respect to step vii.

Step xiii

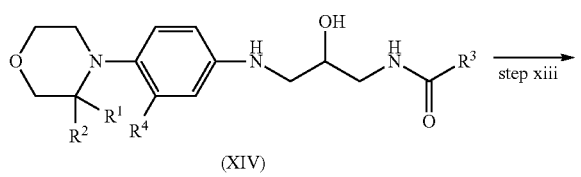

In step xiii, the compound having the formula (XIV) is cyclized to provide a compound having the formula (X). The same reaction conditions as discussed above with respect to step v apply for this reaction.

In route A, the compound having the formula (X) is prepared via a novel methylisobutylketone derivative. This reaction route has the advantage that the synthesis of the compound having the formula (VIII) can be performed as a one-pot reaction.

In route B, the preparation of the compound having the formula (X) is conducted via a hexamethylenetetramine derivative. An improvement of this route can be achieved by replacing the leaving group $X^1$, such as Cl, by a more active leaving group $X^1$, such as I, because replacing the first leaving group by the more active second leaving group reduces the reaction time and increases the quality and yields of the product.

If desired or necessary, any of the above mentioned reactions can be conducted under an inert atmosphere such as a nitrogen atmosphere or a noble gas atmosphere (e.g., argon).

All of the reactions mentioned above can be conducted at ambient pressure or other pressures such as a pressure in the range of about 50 kPa to about 500 kPa. Typically, they will be conducted at ambient pressure.

The present invention is illustrated by the following non-limiting examples.

EXAMPLES

Example 1

(R)-4-Chloromethyl-[1,3,2]dioxathiolane-2-oxide

Under an atmosphere of nitrogen to a solution of 28.12 g of (S)-3-chloro-1,2-propanediol (MW=110.54; 1 eq.) in 600 mL of methylenechloride were added dropwise 30.26 g of thionylchloride (MW=118.97; 1 eq.). After stirring for one hour at room temperature, the reaction mixture was concentrated in vacuo to a mass of 39.93 g. The resulting cyclic sulfite was used in the following step without further purification.

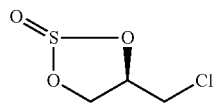

$^1$H-NMR (CDCl$_3$, 300MHz) □□□(ppm)=3.52-3.99 (m, CH$_2$Cl, 2H), 4.46-4.54 (m, CH$_2$O, 0.55H), 4.66-4.88 (m, CH$_2$O, CHO, 1.90H), 5.12-5.21 (m, CHO, 0.55H).

$^{13}$C-NMR (CDCl$_3$, 300MHz) □ (ppm)=42.80, 43.92, 69.53, 71.02, 79.31, 81.23.

Example 2

(R)-4-Chloromethyl-[1,3,2]dioxathiolane 2,2-dioxide (CDHP-Sulfate)

To a solution of 15.78 g of (R)-4-chloromethyl-[1,3,2] dioxathiolane 2,2-dioxide (MW=156.59; 1 eq.) in 64 mL of methylenechloride and 79.5 mL of water were added 17.8 mg of RuCl$_3$.3 H$_2$O (MW=261.47; 0.0007 eq.) The mixture was cooled to 0° C. At this temperature, 85 mL of a solution of sodium hypochlorite (1.7 M; 1.4 eq.) were added in 30 min. After addition of sodium hypochlorite was finished, the reaction mixture was stirred for 15 min at 0° C. Then the layers were separated. The aqueous layer was extracted two times with 64 mL of methylenechloride. To the combined methylenechloride layers were added 1.6 mL of isopropanol and 48 mL of water. After stirring for 5 min, the layers were separated. To the organic layer 1.6 g charcoal were added. After 5 min of stirring, the suspension was filtered and the filtrate was concentrated in vacuo yielding 14.28 g of cyclic sulfate as a colorless oil (MW=172.59). Yield: 82.1%. The resulting cyclic sulfate was used in the following step without further purification.

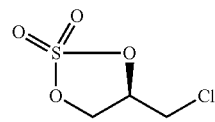

$^1$H-NMR (CDCl$_3$, 300MHz) □□(ppm)=3.76-3.97 (m, CH$_2$Cl, 2H), 4.68 (dd, CH$_2$O, 1H, J 9.2Hz, J 6.4Hz), 4.87 (dd, CH$_2$O, 1H, J 9.2Hz, J 5.9Hz), 5.07-5.20 (m, CHO, 1H).

$^{13}$C-NMR (CDCl$_3$, 300MHz) □ (ppm)=49.77, 70.86, 80.85.

Example 3

Sulfuric acid mono-{(R)-1-chloromethyl-2-[4-(3-oxo-morpholin-4-yl)-phenylamino]-ethyl}ester potassium salt Under an atmosphere of nitrogen to a solution of a 7.11 g of (R)-4-chloromethyl-[1,3,2]dioxathiolane 2,2-dioxide (MW=156.59; 1.38 eq.) in 95 mL of acetonitrile were added 6.34 g of 4-(4-aminophenyl)-morpholin-3-one (APMO) (MW=192.22; 1 eq.) and 3.29 g (MW=138.21; 0.72 eq.) of potassium carbonate. The reaction mixture was stirred for 24 h at room temperature. Then the resulting suspension was cooled to 0° C. After stirring for at least 2 h at this temperature, the product was isolated by filtration and the filter cake was washed with 50 mL of acetonitrile. After drying in vacuo at 30° C., 12.09 g of the crystalline title compound (MW=402.90) were isolated. Yield=91.0%.

m.p.: 147° C.

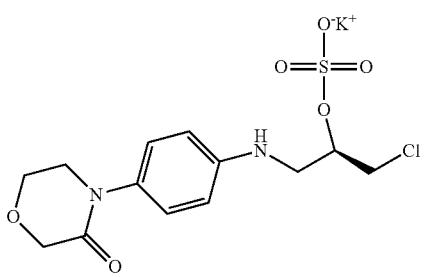

$^1$H-NMR (DMSO-d6, 300Mz) ☐☐☐(ppm)=2.70 (m, CH$_2$, 2H), 3.61 (dd, CH$_2$, 2H, J 4.7, J 5.7Hz), 3.81 (dd, CH$_2$, 2H, J 2.1Hz, J 4.3Hz), 3.92 (dd, CH$_2$, 2H, J 4.7Hz, J 6.2Hz), 4.14 (s, CH$_2$, 2H), 4.44 (m, CHO, 1H), 5.78 (t, NH, 1H), 6.62 (d, CH, 2H, J 8.9Hz), and 7.04 (d, CH, 2H, J 8.9Hz).

$^{13}$C-NMR (DMSO-d6, 300Mz) ☐ (ppm)=44.81, 46.26, 50.43, 64.43, 68.59, 112.27, 127.37, 131.34, 148.02, 166.68.

Example 4

4-[4-((R)-3-Chloro-2-hydroxy-propylamino)-phenyl]-morpholin-3-one

Under an atmosphere of nitrogen to a solution of a 14.22 g of (R)-4-chloromethyl-[1,3,2]dioxathiolane 2,2-dioxide (MW=156.59; 1.37 eq.) in 190 mL of methylenechloride were added 12.68 g of 4-(4-amino-phenyl)-morpholin-3-one (APMO) (MW=192.22; 1 eq.) and 9.2 g (MW=101.12; 1.37 eq.) of triethylamine. The reaction mixture was stirred for 24 h at room temperature. Then the resulting suspension was concentrated in vacuo and the concentrate was dissolved in 400 mL of acetonitrile. 38 g of methane sulfonic acid (MW=96.11; 6.0 eq.). and 7.9 g of water (MW=18.02; 9.0 eq.) were added and the solution were stirred at ambient temperature. After stirring for 5 h, the reaction mixture was neutralized by addition of 50 g of sodium hydrogencarbonate (MW=84.01; 9.0 eq.). The resulting suspension was filtered and the cake washed with 200 mL of acetonitrile. The combined acetonitrile layers were concentrated in vacuo. To the concentrate were added 260 mL of 2-propanol and the mixture was stirred for 1 h at ambient temperature. The resulting slurry was cooled to 0° C. After stirring for at least 2 h at this temperature, the product was isolated by filtration and the filter cake was washed with 50 mL of 2-propanol. After drying in vacuo at 30° C., 11.75 g of the crystalline title compound (MW=284.75) were isolated. Yield=62.6%.

m.p.: 146° C.

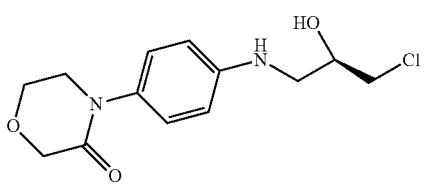 [SMILES: O=C1COCCN1c1ccc(NC[C@@H](O)CCl)cc1]

$^1$H-NMR (DMSO-d6, 300Mz) ☐☐☐(ppm)=2.99-3.09 (m, CH$_2$, 1H), 3.13-3.23 (m, CH$_2$, 1H), 3.56-3.64 (m, CH$_2$, 2H), 3.69 (dd, CH$_2$, 1H, J 4.7, J 5.7Hz), 3.84 (m, CH, 1H), 3.92 (dd, CH$_2$, 2H, J 4.5Hz, J 11.2Hz), 4.14 (s, CH$_2$CO, 2H), 5.36 (d, OH, 1H, J 5.2Hz), 5.73 (t, NH, 1H, J 5.8Hz), 6.60 (d, CH, 2H, J 8.9Hz), and 7.03 (d, CH, 2H, J 8.9Hz).

$^{13}$C-NMR (DMSO-d6, 300Mz) ☐☐(ppm)=44.81, 46.26, 50.43, 64.43, 68.59, 112.27, 127.37, 131.34, 148.02, 166.68.

Example 5

4-[4-[(5R)-5-(Chloromethyl)-2-oxo-3-oxazolidinyl]phenyl]-3-morpholinone

Under an atmosphere of nitrogen to a solution of 10.53 g of 4-[4-((R)-3-chloro-2-hydroxy-propylamino)-phenyl]-morpholin-3-one (MW=284.75; 1 eq.) in 150 mL acetonitrile were added 7.84 g of N,N'-carbonyldiimidazole (MW=162.15; 1.3). The resulting reaction mixture was stirred for 3 h at room temperature. Then the resulting slurry was concentrated in vacuo and to the concentrate 150 mL of 2-propanol were added. After stirring for 1 h at ambient temperature, the crystal suspension was cooled to 0° C. After stirring for at least 2 h at this temperature, the product was isolated by filtration and the filter cake was washed with 50 mL of 2-propanol. After drying in vacuo at 30° C., 11.75 g of the crystalline title compound were isolated. Yield=74.8%.

mp: 148° C.

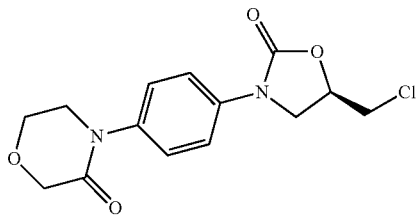 [SMILES: O=C1COCCN1c1ccc(N2C[C@H](CCl)OC2=O)cc1]

$^1$H-NMR (DMSO-d6, 300Mz) ☐☐☐(ppm)=3.71 (t, CH, 1H, J 5.0Hz), 3.84 (dd, CH$_2$, 1H, J 5.7, J 9.2Hz), 2.99-3.09 (m, CH$_2$, 1H), 3.13-3.23 (m, CH$_2$, 1H), 3.56-3.64 (m, CH$_2$, 2H), 3.69 (dd, CH$_2$, 1H, J 4.7, J 5.7Hz), 3.92-4.07 (m, CH$_2$, 3H), 3.92 (dd, CH$_2$, 2H, J 4.5Hz, J 11.2Hz), 4.14 (s, CH$_2$CO, 2H), 4.22 (t, CH, 1H, J 9.2Hz), 5.36 (d, OH, 1H, J 5.2Hz), 5.73 (t, NH, 1H, J 5.8Hz), 7.42 (d, CH, 2H, J 8.9Hz), 7.59 (d, CH, 2H, J 8.9Hz).

$^{13}$C-NMR (DMSO-d6, 300Mz) ☐☐(ppm)=44.81, 46.26, 50.43, 64.43, 68.59, 112.27, 127.37, 131.34, 148.02, 166.68.

Example 6

4-[4-[(5R)-5-(Iodomethyl)-2-oxo-3-oxazolidinyl]phenyl]-3-morpholinone

Under an atmosphere of nitrogen to a solution of 1.00 g of 4-[4-[(5R)-5-(chloromethyl)-2-oxo-3-oxazolidinyl]phenyl]-3-morpholinone (MW=310.74; 1 eq.) in 5.3 mL sulfolane were added 0.97 g of sodium iodide (MW=149.89; 2 eq.). The resulting reaction mixture was stirred for 20 h at 110° C. Then the resulting slurry was cooled to room temperature and diluted with 30 mL of water. After stirring for 1 h at ambient temperature, the crystal suspension was isolated by filtration and the filter cake was washed with 20 mL of water. After drying in vacuo at 30° C., 1.05 g of the crystalline title compound (MW=402.19) were isolated. Yield=81.4%.

mp.: 157° C.

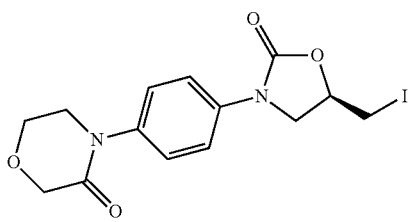 [SMILES: O=C1COCCN1c1ccc(N2C[C@H](CI)OC2=O)cc1]

¹H-NMR (DMSO-d6, 300Mz) ☐☐☐(ppm)=3.71 (t, CH, 1H, J 5.0Hz), 3.84 (dd, CH₂, 1H, J 5.7, J 9.2Hz), 2.99-3.09 (m, CH₂, 1H), 3.13-3.23 (m, CH₂, 1H), 3.56-3.64 (m, CH₂, 2H), 3.69 (dd, CH₂, 1H, J 4.7, J 5.7Hz), 3.92-4.07 (m, CH₂, 3H), 3.92 (dd, CH₂, 2H, J 4.5Hz, J 11.2Hz), 4.14 (s, CH₂CO, 2H), 4.22 (t, CH, 1H, J 9.2Hz), 5.36 (d, OH, 1H, J 5.2Hz), 5.73 (t, NH, 1H, J 5.8Hz), 7.42 (d, CH, 2H, J 8.9Hz), 7.59 (d, CH, 2H, J 8.9Hz).

¹³C-NMR (DMSO-d6, 300Mz) ☐ (ppm)=44.81, 46.26, 50.43, 64.43, 68.59, 112.27, 127.37, 131.34, 148.02, 166.68.

Example 7

1-{(R)-2-oxo-3-[4-(3-oxo-morpholin-4-yl)-phenyl]-oxazolidin-5-ylmethyl}-3,5,7-triaza-1-azonia-tricyclo[3.3.1.1*3,7*]decane; iodide Under an atmosphere of nitrogen to a solution of 0.403 g of 4-[4-[(5R)-5-(iodomethyl)-2-oxo-3-oxazolidinyl]phenyl]-3-morpholinone (MW=402.19; 1 eq.) in 2.1 mL sulfolane were added 0.154 g of hexamethylenetetramine (MW=149.89; 2 eq.). The resulting reaction mixture was stirred for 3 days at 50° C. Then the resulting slurry was cooled to room temperature and diluted with 10 mL of methylenechloride. After stirring for 1 h at ambient temperature, the crystal suspension was isolated by filtration and the filter cake was washed with 10 mL of methylenechloride and 10 mL of acetonitrile. After drying in vacuo at 30° C., 0.329 g of the crystalline title compound (MW=542.38) were isolated. Yield=60.6%.

mp.: 203° C.

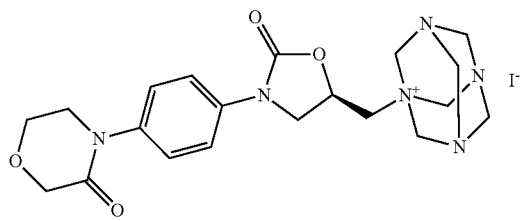 [SMILES: O=C1COCCN1c1ccc(N2C[C@H](C[N+]34CN5CN(CN(C5)C3)C4)OC2=O)cc1 ; [I-]]

Example 8

1-{(R)-2-oxo-3-[4-(3-oxo-morpholin-4-yl)-phenyl]-oxazolidin-5-ylmethyl}-3,5,7-triaza-1-azonia-tricyclo[3.3.1.1*3,7*]decane; iodide (PMO-HMTAOXZ.HI)

Under an atmosphere of nitrogen to a solution of 0.403 g of 4-[4-[(5R)-5-(iodomethyl)-2-oxo-3-oxazolidinyl]phenyl]-3-morpholinone (MW=402.19; 1 eq.) in 2.1 mL sulfolane were added 0.154 g of hexamethylenetetramine (MW=149.89; 2 eq.). The resulting reaction mixture was stirred for 24 h at 60° C. Then the resulting slurry was cooled to room temperature and diluted with 10 mL of acetonitrile. After stirring over night at ambient temperature, the crystal suspension was isolated by filtration and the filter cake was washed with 10 mL of acetonitrile. After drying in vacuo at 30° C., 0.279 g of the crystalline title compound (MW=542.38) were isolated. Yield=51.4%.

mp.: 203° C.

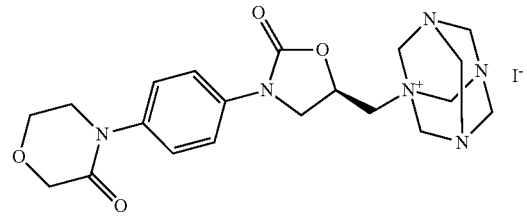 [SMILES: O=C1COCCN1c1ccc(N2C[C@H](C[N+]34CN5CN(CN(C5)C3)C4)OC2=O)cc1 ; [I-]]

¹H-NMR (DMSO-d6, 300Mz) ☐☐☐(ppm)=3.71 (t, CH, 1H, J 5.0Hz), 3.84 (dd, CH₂, 1H, J 5.7, J 9.2Hz), 2.99-3.09 (m, CH₂, 1H), 3.13-3.23 (m, CH₂, 1H), 3.56-3.64 (m, CH₂, 2H), 3.69 (dd, CH₂, 1H, J 4.7, J 5.7Hz), 3.92-4.07 (m, CH₂, 3H), 3.92 (dd, CH₂, 2H, J 4.5Hz, J 11.2Hz), 4.14 (s, CH₂CO, 2H), 4.22 (t, CH, 1H, J 9.2Hz), 5.36 (d, OH, 1H, J 5.2Hz), 5.73 (t, NH, 1H, J 5.8Hz), 7.42 (d, CH, 2H, J 8.9Hz), 7.59 (d, CH, 2H, J 8.9Hz).

¹³C-NMR (DMSO-d6, 300Mz) ☐☐(ppm)=44.81, 46.26, 50.43, 64.43, 68.59, 112.27, 127.37, 131.34, 148.02, 166.68.

Example 9

[4-((S)-5-Aminomethyl-2-oxo-oxazolidin-3-yl)-phenyl]-morpholin-3-one; hydrochloride Under an atmosphere of nitrogen to a suspension of 100 mg of 1-{(R)-2-oxo-3-[4-(3-oxo-morpholin-4-yl)-phenyl]-oxazolidin-5-ylmethyl}-3,5,7-triaza-1-azonia-tricyclo[3.3.1.1*3,7*]decane iodide (MW=542.38; 1 eq.) in 2 mL of ethanol were added 100 mg of conc. hydrochloric acid (MW=36.46; 5 eq.) and 950 mg of water. The reaction mixture was warmed to 50° C. and stirring was continued for 2 h. Then the reaction mixture was cooled to 0° C. After stirring for 1 h at 0° C., the crystals were isolated by filtration, washed with 10 mL of ethanol and the wet product was dried in vacuo at 30° C. The yield of isolated crystalline hydrochloride of the title compound was 20 mg (approx. 33.1%). mp: 210-220° C.

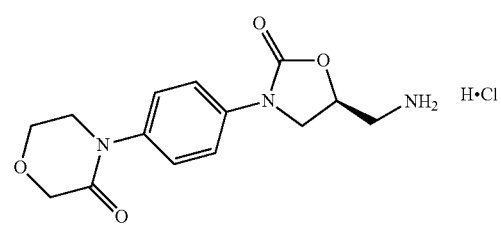

Example 10

5-Chlor-N-({(5S)-2-oxo-3-[4-(3-oxo-4-morpholinyl)phenyl]-1,3-oxazolidin-5-yl}methyl)-2-thiophenecarboxamide Under an atmosphere of nitrogen to a suspension of 0.164 g of 4-((S)-5-aminomethyl-2-oxo-oxazolidin-3-yl)-phenyl-morpholin-3-one hydrochloride (MW=327.77; 1 eq.) in 7 mL of acetonitrile were added 0.101 g of triethylamine (MW=101.12; 2.0 eq.). After stirring for 10 min at room temperature, the suspension was cooled to 0° C. and then 0.091 g of 5-chloro-thiophene-2-carbonyl chloride (MW=181.04; 1.0 eq.) were added. After stirring for 80 min at 0° C., the resulting slurry was filtered and the cake washed with 5 mL of acetonitrile and 5 mL of water. After drying in vacuo at 30° C., 0.180 g of the title compound in the form of a white crystalline powder was isolated. Yield=82.7%.

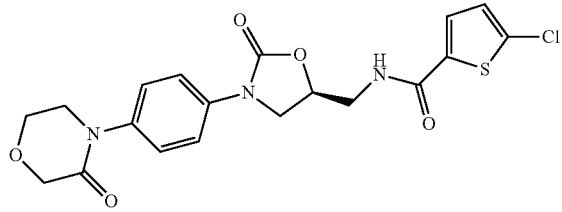 [SMILES: O=C(NC[C@H]1CN(c2ccc(N3CCOCC3=O)cc2)C(=O)O1)c1ccc(Cl)s1]

Example 11

4-[4-((R)-3-Chloro-2-hydroxy-propylamino)-phenyl]-morpholin-3-one (One-Pot Procedure)

Under an atmosphere of nitrogen to a solution of 28.12 g of (S)-3-chloro-1,2-propanediol (MW=110.54; 1 eq.) in 600 mL of methylenechloride were added dropwise 30.26 g of thionylchloride (MW=118.97; 1 eq.). After stirring for 1 h at room temperature, the reaction mixture was concentrated in vacuo to a mass of 255 g. To the concentrate of (R)-4-chloromethyl-[1,3,2]dioxathiolane 2,2-dioxide (MW=156.59; 1 eq.) were added 200 mL of water and 45 mg of RuCl$_3$.3 H$_2$O (MW=261.47; 0.0007 eq.) The mixture was cooled to 0° C. At this temperature, 215 mL of a cold solution of sodium hypochlorite (1.7 M; 1.4 eq.) were added in 60 min. After addition of sodium hypochlorite was finished, the reaction mixture was stirred for 15 min at 0° C. Then the layers were separated. The aqueous layer was extracted twice with 160 mL of methylenechloride. To the combined methylenechloride layers were added 4 mL of isopropanol and 120 mL of water. After stirring for 5 min the layers were separated. To the organic layer, 1.6 g charcoal were added. After 5 min of stirring, the suspension was filtered. To the filtrate were added 32.09 g of 4-(4-aminophenyl)-morpholin-3-one (APMO) (MW=192.22; 0.66 eq.) and 23.28 g (MW=101.12; 0.9 eq.) of triethylamine. The reaction mixture was stirred for 24 h at room temperature. Then the resulting suspension was concentrated in vacuo and the concentrate was dissolved in 1000 mL of acetonitrile. 96 g of methane sulfonic acid (MW=96.11; 3.9 eq.) and 20 g of water (MW=18; 4.4 eq.) were added and the solution was stirred at ambient temperature. After stirring for 5 h, the reaction mixture was neutralized by addition of 127 g of sodium hydrogencarbonate (MW=84.01; 5.9 eq.). The resulting suspension was filtered and the cake washed with 500 mL of acetonitrile. The combined acetonitrile layers were concentrated in vacuo. To the concentrate were added 660 mL of 2-propanol and the mixture was stirred for 1 h at ambient temperature. The resulting slurry was cooled to 0° C. After stirring for at least 2 h at this temperature, the product was isolated by filtration and the filter cake was washed with 125 mL of 2-propanol. After drying in vacuo at 30° C., 29.73 g of the crystalline title compound were isolated. Yield=41.0%.

m.p.: 146° C.

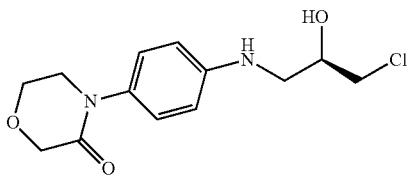 [SMILES: O=C1COCCN1c1ccc(NC[C@@H](O)CCl)cc1]

Example 12

4-[4-((R)-3-Amino-2-hydroxy-propylamino)-phenyl]-morpholin-3-one hydrochloride 8.95 g of 4-[4-((R)-3-chloro-2-hydroxy-propylamino)-phenyl]-morpholin-3-one (MW=284.75; 1 eq.) were added to 189 g of conc. aqueous ammonia (MW=17.03; 88 eq.). The reaction mixture was stirred for 4 h at room temperature. Then 0.9 g of charcoal were added and after 10 min of stirring, the suspension was filtered and the cake washed with 30 mL of water. Filtrate and wash water were combined and concentrated in vacuo. To the residue were added 50 mL of ethanol. The resulting suspension was stirred for 1 h at ambient temperature and then cooled to 0° C. After stirring for at least 2 h at this temperature, the product was isolated by filtration and the filter cake was washed with 25 mL of ethanol. After drying in vacuo at 30° C., 5.73 g of the crystalline title compound were isolated. Yield=60.4%.

m.p.: 180-190° C.

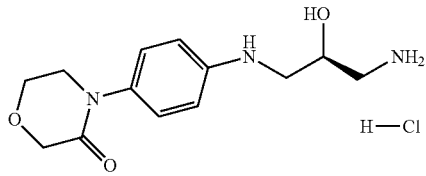

$^1$H-NMR (DMSO-d6+TFA-d1, 300Mz) ☐☐☐(ppm)= 2.87-2.97 (m, CH$_2$, 1H), 3.05-3.13 (m, CH$_2$, 1H), 3.39-3.58 (m, CH$_2$, 2H), 3.71 (m, CH$_2$, 2H), 4.00 (m, CH$_2$, 2H), 4.09 (m, CH, 1H), 4.26 (s, CH$_2$CO, 2H), 7.48 (m, CH, 4H).

Example 13

4-[4-((R)-3-Amino-2-hydroxy-propylamino)-phenyl]-morpholin-3-one hydrochloride 30.00 g of 4-[4-((R)-3-chloro-2-hydroxy-propylamino)-phenyl]-morpholin-3-one (MW=284.75; 1 eq.) were added to 634 g of conc. aqueous ammonia (MW=17.03; 88 eq.). The reaction mixture was stirred for 4 h at room temperature. Then 3.0 g of charcoal were added and after 10 min of stirring, the suspension was filtered and the cake was washed with 90 mL of water. Filtrate and wash water were combined and concentrated in vacuo to a mass of 37 g. To the residue were added 107 mL of ethanol. The resulting suspension was stirred for 1 h at ambient temperature and then cooled to 0° C. After stirring for at least 2 h at this temperature, the product was isolated by filtration and the filter cake was washed with 75 mL of ethanol. After drying in vacuo at 30° C., 24.89 g of the crystalline title compound were isolated. Yield=78.3%.

m.p.: 180-190° C.

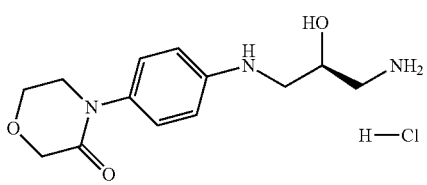

$^1$H-NMR (DMSO-d6+TFA-d1, 300Mz) □□□ (ppm) =2.87-2.97 (m, CH$_2$, 1H), 3.05-3.13 (m, CH$_2$, 1H), 3.39-3.58 (m, CH$_2$, 2H), 3.71 (m, CH$_2$, 2H), 4.00 (m, CH$_2$, 2H), 4.09 (m, CH, 1H), 4.26 (s, CH$_2$CO, 2H), 7.48 (m, CH, 4H).

Example 14

4-[4-((R)-3-Amino-2-hydroxy-propylamino)-phenyl]-morpholin-3-one hydrochloride 30.00 g of 4-[4-((R)-3-chloro-2-hydroxy-propylamino)-phenyl]-morpholin-3-one (CHP-APMO) (MW=284.75; 1 eq.) were added to 1298 g of conc. aqueous ammonia (MW 17.03; 181 eq.). The reaction mixture was stirred for 2.5 h at room temperature. Then 3.0 g of charcoal were added and after 10 min of stirring, the suspension was filtered and the cake was washed with 90 mL of water. Filtrate and wash water were combined and concentrated in vacuo to a mass of 37 g. To the residue were added 107 mL of ethanol. The resulting suspension was stirred for 1 h at ambient temperature and then cooled to 0° C. After stirring for at least 2 h at this temperature, the product was isolated by filtration and the filter cake was washed with 75 mL of ethanol. After drying in vacuo at 30° C., 23.98 g of the crystalline title compound were isolated. Yield=75.4%.

m.p.: 180-190° C.

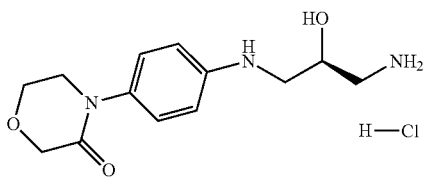

$^1$H-NMR (DMSO-d6+TFA-d1, 300Mz) □□□(ppm) =2.87-2.97 (m, CH$_2$, 1H), 3.05-3.13 (m, CH$_2$, 1H), 3.39-3.58 (m, CH$_2$, 2H), 3.71 (m, CH$_2$, 2H), 4.00 (m, CH$_2$, 2H), 4.09 (m, CH, 1H), 4.26 (s, CH$_2$CO, 2H), 7.48 (m, CH, 4H).

Example 15

4-[4-((R)-3-Amino-2-hydroxy-propylamino)-phenyl]-morpholin-3-one 30.00 g of 4-[4-((R)-3-chloro-2-hydroxy-propylamino)-phenyl]-morpholin-3-one (MW=284.75; 1 eq.) were added to 1298 g of conc. aqueous ammonia (MW=17.03; 88 eq.). The reaction mixture was stirred for 2.5 h at room temperature. Then 3.0 g of charcoal were added and after 10 min of stirring, the suspension was filtered and the cake was washed with 90 mL of water. Filtrate and wash water were combined and concentrated in vacuo to a mass of 100 g. The concentrate was alkalized by addition of 21.84 g of potassium carbonate (MW=138.21; 1.5 eq.) and to the alkaline solution were added 200 mL of methylenechloride. After 10 min of stirring, the layers were separated and the aqueous layer was extracted once more with 100 mL of methylenechloride. The organic layers were combined and concentrated in vacuo. To the residue were added 150 mL of methyl tert-butyl ether and the resulting suspension was stirred for at least one hour at ambient temperature. Then the crystalline product was isolated by filtration and the filter cake was washed with 75 mL of methyl tert-butyl ether. After drying in vacuo at 30° C., 21.08 g of the crystalline title compound (MW 265.31) were isolated. Yield=75.4%.

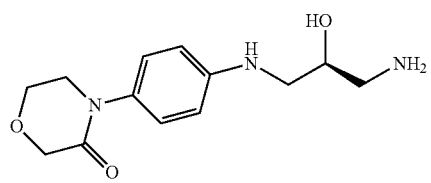 [SMILES: NC[C@H](O)CNc1ccc(N2CCOCC2=O)cc1]

$^1$H-NMR (DMSO-d6+TFA-d1, 300Mz) □□□(ppm) =2.87-2.97 (m, CH$_2$, 1H), 3.05-3.13 (m, CH$_2$, 1H), 3.39-3.58 (m, CH$_2$, 2H), 3.71 (m, CH$_2$, 2H), 4.00 (m, CH$_2$, 2H), 4.09 (m, CH, 1H), 4.26 (s, CH$_2$CO, 2H), 7.48 (m, CH, 4H).

Example 16

[4-((S)-5-Aminomethyl-2-oxo-oxazolidin-3-yl)-phenyl]-morpholin-3-one; hydrochloride 30.00 g of 4-[4-((R)-3-chloro-2-hydroxy-propylamino)-phenyl]-morpholin-3-one (MW=284.75; 1 eq.) were added to 1298 g of conc. aqueous ammonia (MW=17.03; 181 eq.). The reaction mixture was stirred for 2.5 h at room temperature. Then 3.0 g of charcoal were added and after 10 min of stirring, the suspension was filtered and the cake was washed with 90 mL of water. Filtrate and wash water were combined and concentrated in vacuo to a mass of 100 g. The concentrate was alkalized by addition of 21.84 g of potassium carbonate (MW=138.21; 1.5 eq.) and to the alkaline solution 200 mL of methylisobutylketone were added. After 10 min of stirring, the layers were separated and the aqueous layer was extracted once more with 100 mL of methylisobutylketone. The organic layers were combined and heated to reflux temperature. The formed water was removed by azeotropic distillation. After refluxing for 2 h and removing water by azeotropic distillation, the reaction mixture was cooled to room temperature and then 25.63 g of N,N'-carbonyldiimidazol (MW=162.15; 1.5 eq.) were added. After stirring at ambient temperature for 15 hours, the reaction mixture was filtered. To the clear filtrate were added 5 mL of 6 M hydrochloric acid (1.5 eq.) and 50 mL of water and stirring was continued for 1 h. Then the mixture was concentrated in vacuo. To the solid residue were added 5.5 mL of water and 22 mL of ethanol. The resulting slurry was stirred for 1 h at ambient temperature and then cooled to 0° C. After stirring in an ice bath for at least 2 h, the crystals were isolated by filtration, washed with 10 mL of ethanol and the wet product was dried in vacuo at 30° C. The yield of isolated crystalline hydrochloride (MW=327.77) of the title compound was 25.40 g (approx. 73.5% by theory).

33

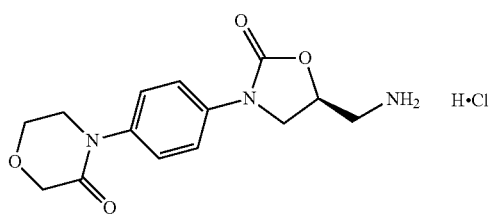 [SMILES: NC[C@H]1CN(c2ccc(N3CCOCC3=O)cc2)C(=O)O1 ; "H·Cl"]

¹H-NMR (DMSO-d6, 300Mz) □□(ppm)=3.21-3.26 (m, NCH₂, 2H), 3.56-3.64 (m, CH₂, 2H), 3.72 (m, CH₂, 2H), 3.87-4.00 (m, CH₂, CH, 3H), 4.20 (s, CH₂CO, 2H), 3.21 (m, CH₂, 1H), 4.98 (m, CH, 1H), 7.56 (d, CH, 2H, J 9.0Hz), 7.43 (d, CH, 2H, J 9.0Hz), 8.49 (3, NH, 3H).

¹³C-NMR (DMSO-d6, 300Mz) □□(ppm)=48.10, 49.89, 55.99, 64.30, 68.51, 70.27, 119.47, 126.88, 137.14, 138.06, 154.48, 167.02.

Example 19

[4-((S)-5-Aminomethyl-2-oxo-oxazolidin-3-yl)-phenyl]-morpholin-3-one; hydrochloride Under an atmosphere of nitrogen to a suspension of 2.00 g of 4-[4-((R)-3-amino-2-hydroxy-propylamino)-phenyl]-morpholin-3-one hydrochloride (MW=301.78; 1 eq.) in 100 mL of methylisobutylketone were added 3.85 g of potassium carbonate (MW=138.21; 4.2 eq.) and the suspension was heated to reflux. The formed water was removed by azeotropic distillation. After refluxing for 4 h and removing water by azeotropic distillation, the reaction mixture was cooled to room temperature and then 1.61 g of N,N'-carbonyldiimidazol (MW=162.15; 1.5 eq.) were added. After stirring at ambient temperature for 15 h, the reaction mixture was filtered. To the clear filtrate were added 5 mL of 6 M hydrochloric acid (1.5 eq.) and 50 mL of water and stirring was continued for 1 h. Then the mixture was concentrated in vacuo. To the solid residue were added 5.5 mL of water and 22 mL of 2-propanol. The resulting slurry was stirred for 1 h at ambient temperature and then cooled to 0° C. After stirring in an ice bath for at least 2 h, the crystals were isolated by filtration, washed with 10 mL of 2-propanol and the wet product was dried in vacuo at 30° C. The yield of isolated crystalline hydrochloride (MW=327.77) of the title compound was 1.74 g (80.1%).

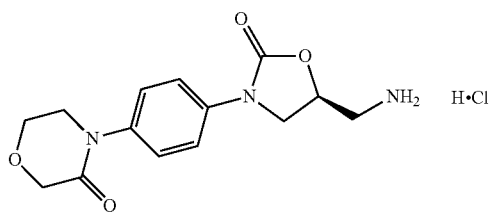 [SMILES: NC[C@H]1CN(c2ccc(N3CCOCC3=O)cc2)C(=O)O1 ; "H·Cl"]

¹H-NMR (DMSO-d6, 300Mz) □□(ppm)=3.21-3.26 (m, NCH₂, 2H), 3.56-3.64 (m, CH₂, 2H), 3.72 (m, CH₂, 2H), 3.87-4.00 (m, CH₂, CH, 3H), 4.20 (s, CH₂CO, 2H), 3.21 (m, CH₂, 1H), 4.98 (m, CH, 1H), 7.56 (d, CH, 2H, J 9.0Hz), 7.43 (d, CH, 2H, J 9.0Hz), 8.49 (3, NH, 3H).

¹³C-NMR (DMSO-d6, 300Mz) □ (ppm)=48.10, 49.89, 55.99, 64.30, 68.51, 70.27, 119.47, 126.88, 137.14, 138.06, 154.48, 167.02.

34

Example 20

5-Chloro-thiophene-2-carboxylic acid {(R)-2-hydroxy-3-[4-(3-oxo-morpholin-4-yl)-phenylamino]-propyl}-amide Under an atmosphere of nitrogen to a suspension of 1.65 g of 5-chloro-thiophene-2-carboxylic acid (MW=162.60; 1.2 eq.) in 50 mL of methylenechloride were added 1.62 g N,N'-carbonyldiimidazole (MW=162.15; 1.2 eq.) and the reaction mixture was stirred for 2 h. To the resulting solution of the azolide were added 2.41 g of 4-[4-((R)-3-amino-2-hydroxy-propylamino)-phenyl]-morpholin-3-one hydrochloride (MW=301.78; 1 eq.) and stirring at ambient temperature was continued for 4 h. Then 50 mL of 1 M aqueous hydrochloride were added. After 5 min of stirring, the layers were separated. The organic layer was extracted once more with 25 mL of 1 M hydrochloric acid. The combined aqueous layers were washed with 25 mL of methylenechloride and neutralized by the addition of approx. 15 mL of 5 M sodium hydroxide. The resulting suspension was stirred for 1 h at ambient temperature, then cooled to 0° C. After stirring in an ice bath for 2 h, the precipitate was isolated by filtration, washed with 10 mL of water and the wet product was dried in vacuo at 40° C.

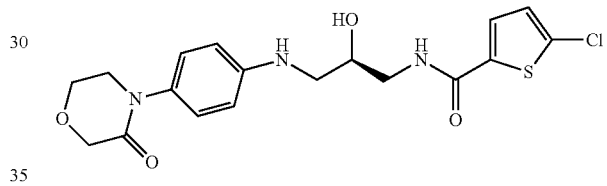

What is claimed:

1. A method for the preparation of a compound having the formula (X), wherein the method comprises the steps of:

Step i: reacting a compound having the formula (I) with a compound having the formula (II) to provide a compound having the formula (III)

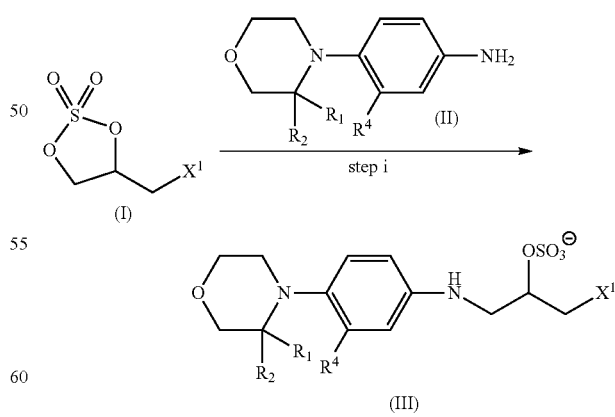

Step ii: converting the sulfate moiety of the compound having the formula (III) into a hydroxy group in the presence of water to provide a compound having the formula (IV)

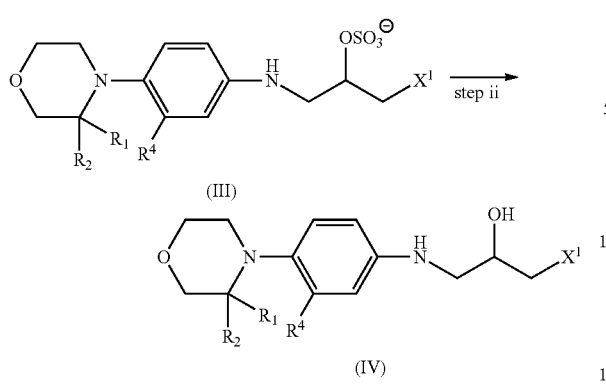

(III)

(IV)

Step iii: replacing the leaving group $X^1$ of the compound having the formula (IV) by $NH_3$ to provide a compound having the formula (V)

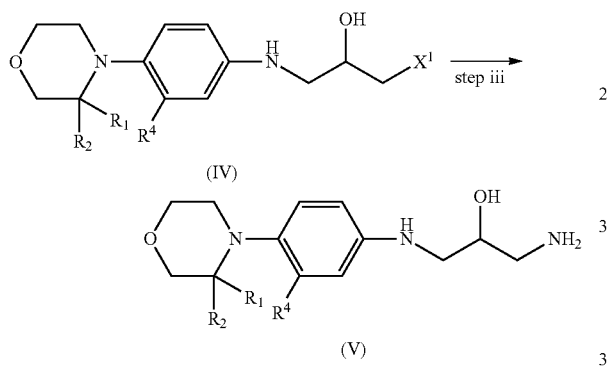

(IV)

(V)

Step iv: reacting the compound having the formula (V) with methylisobutylketone to provide a compound having the formula (VI)

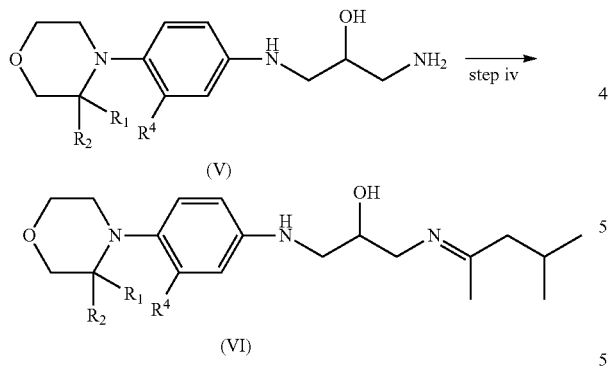

(V)

(VI)

Step v: cyclizing the compound having the formula (VI) to provide a compound having the formula (VII)

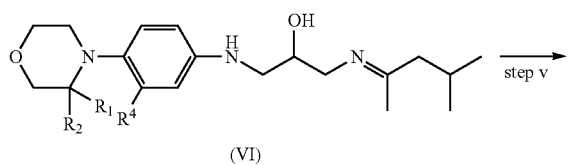

(VI)

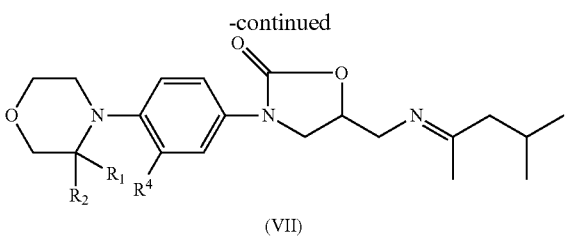

(VII)

Step vi: removing the methylisobutylketone group from the compound having the formula (VII) to provide a compound having the formula (VIII)

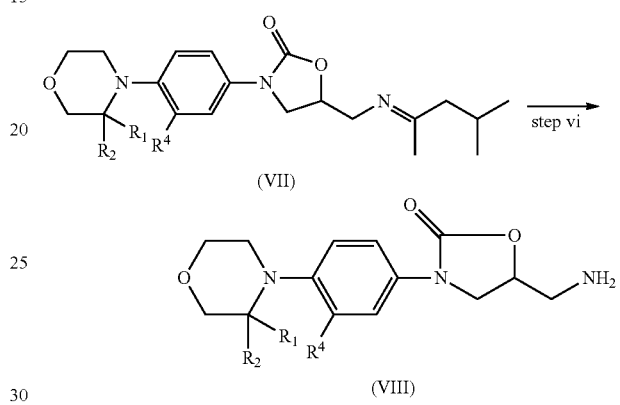

(VII)

(VIII)

Step vii: reacting the compound having the formula (VIII) with a compound having the formula (IX) to provide a compound having the formula (X)

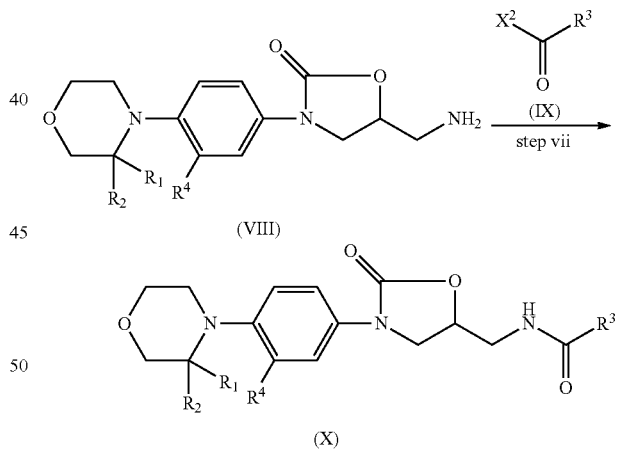

(VIII)

(X)

wherein
$X^1$ is a leaving group;
$X^2$ is a leaving group which can be the same or different than $X^1$;
the moiety $C(R^1)(R^2)$ is C=O or $CH_2$;
$R^3$ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S, wherein the alkyl group, the aryl group and the heterocyclic group can be optionally substituted; and
$R^4$ is H or halogen.

2. The method according to claim 1, wherein the method employs an enantiomerically enriched or enantiomerically pure starting material and which method comprises the steps of:

Step i: reacting a compound having the formula (I) with a compound having the formula (II) to provide a compound having the formula (III)

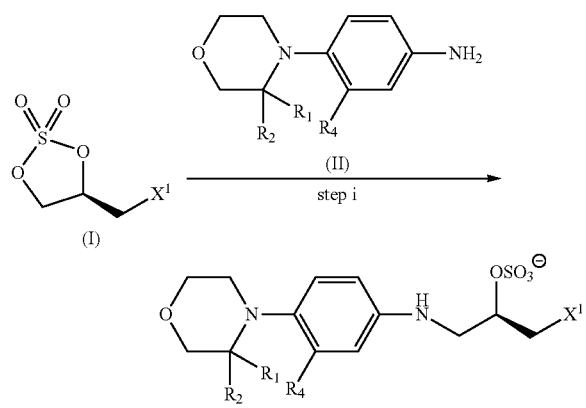

Step ii: converting the sulfate moiety of the compound having the formula (III) into a hydroxy group in the presence of water to provide a compound having the formula (IV)

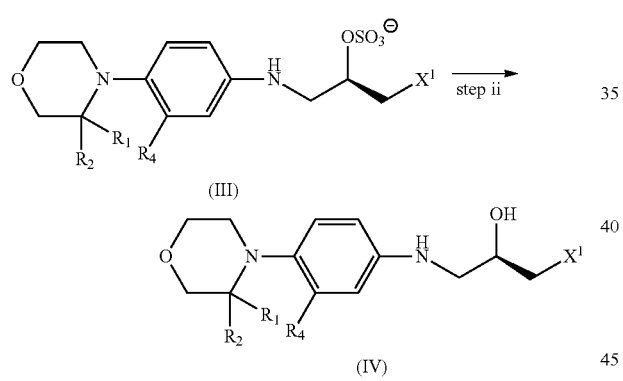

Step iii: replacing the leaving group $X^1$ of the compound having the formula (IV) by $NH_3$ to provide a compound having the formula (V)

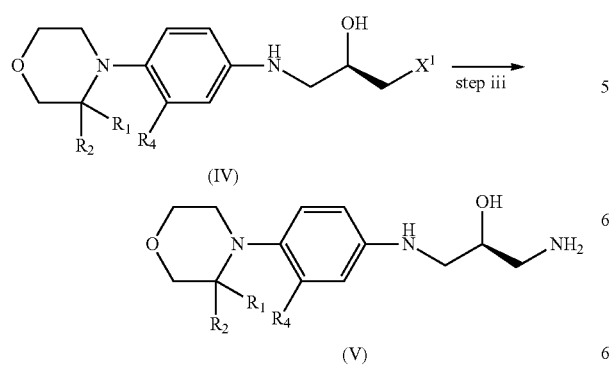

Step iv: reacting the compound having the formula (V) with methylisobutylketone to provide a compound having the formula (VI)

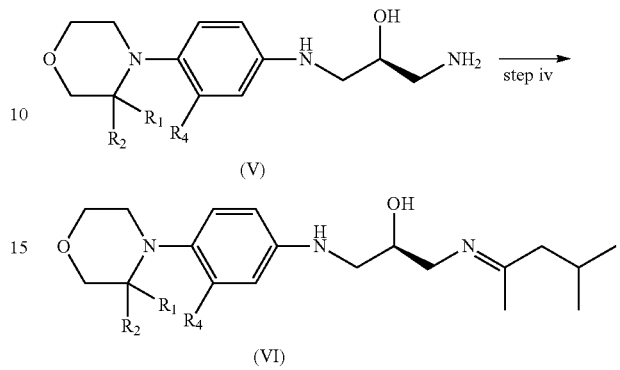

Step v: cyclizing the compound having the formula (VI) to provide a compound having the formula (VII)

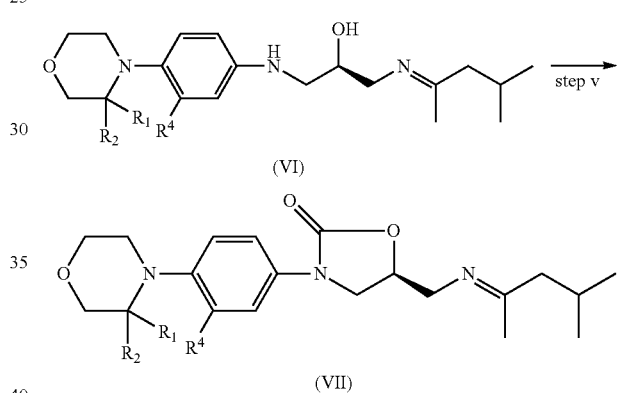

Step vi: removing the methylisobutylketone group from the compound having the formula (VII) to provide a compound having the formula (VIII)

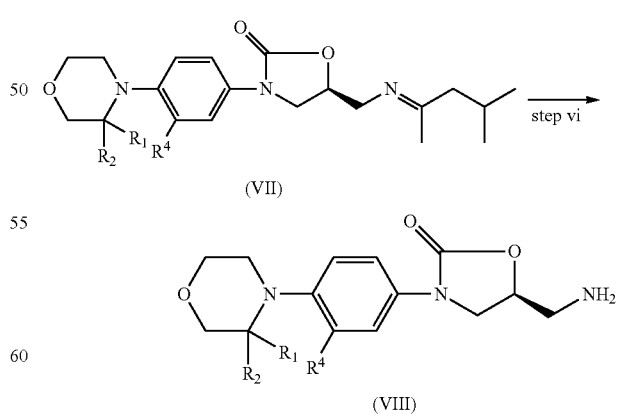

Step vii: reacting the compound having the formula (VIII) with a compound having the formula (IX) to provide a compound having the formula (X)

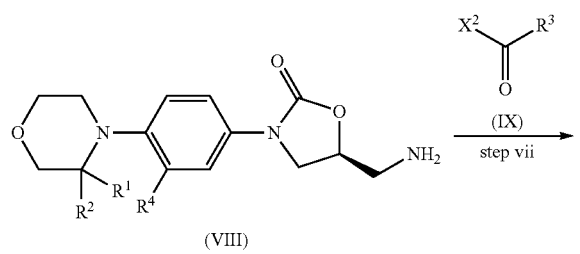

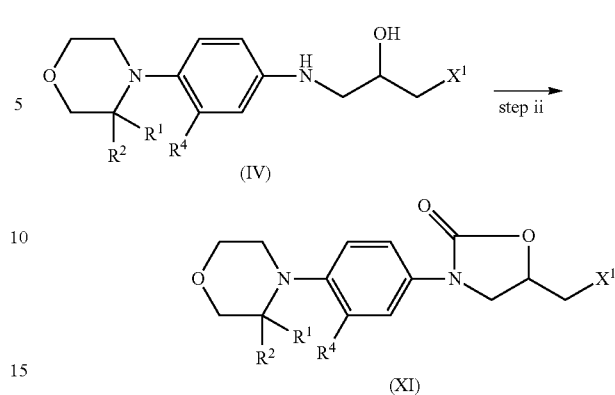

3. A method for the preparation of a compound having the formula (X), wherein the method comprises the steps of:
Step i: reacting a compound having the formula (I) with a compound having the formula (II) to provide a compound having the formula (III)

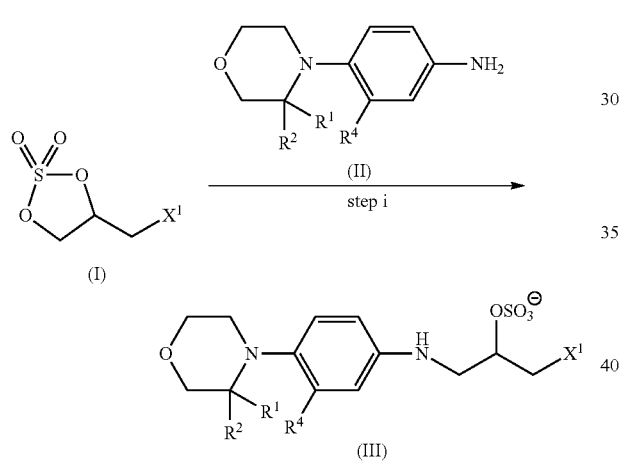

Step ii: converting the sulfate moiety of the compound having the formula (III) into a hydroxy group in the presence of water to provide a compound having the formula (IV)

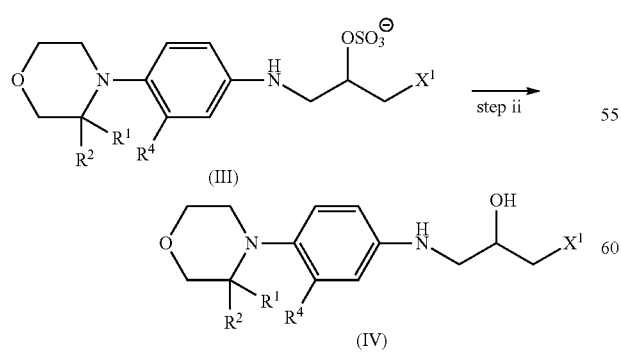

Step viii: cyclizing the compound having the formula (IV) to provide a compound having the formula (XI)

Step ix: optionally replacing the leaving group $X^1$ in the compound having the formula (XI) by a different leaving group $X^1$ to provide a compound having the formula (XII)

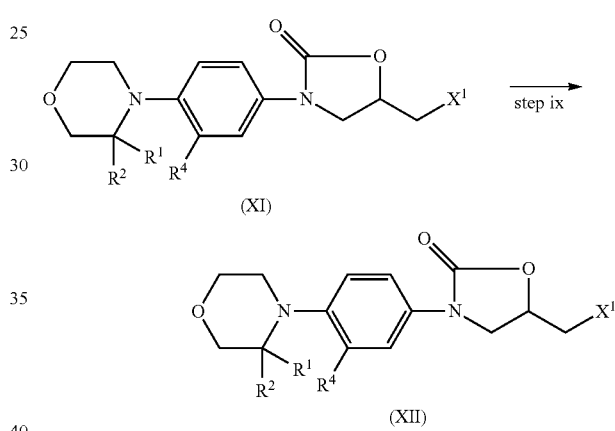

Step x: reacting the compound having the formula (XI) or (XII) with hexamethylenetetramine to provide a compound having the formula (XIII)

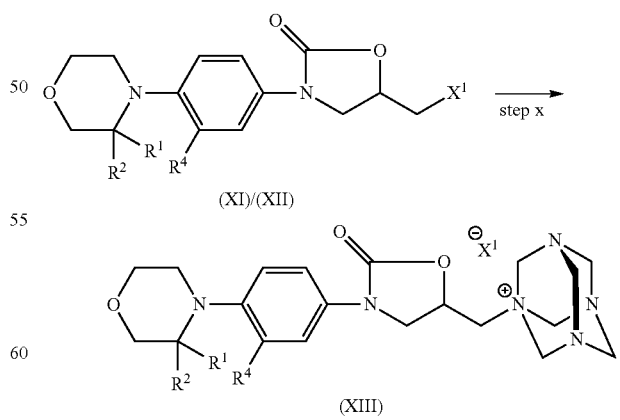

Step xi: removing the hexamethylenetetramine moiety of the compound having the formula (XIII) to provide a compound having the formula (VIII)

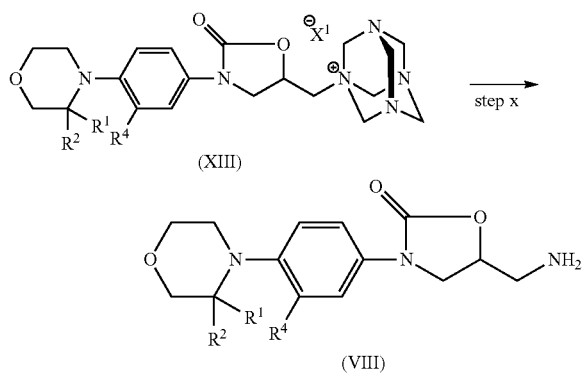

(XIII)

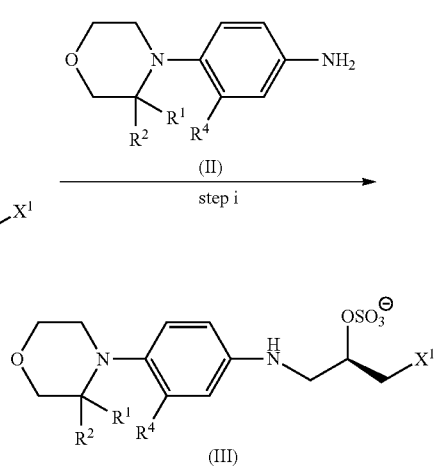

(I)

(II)

Step vii: reacting the compound having the formula (VIII) with a compound having the formula (IX) to provide a compound having the formula (X)

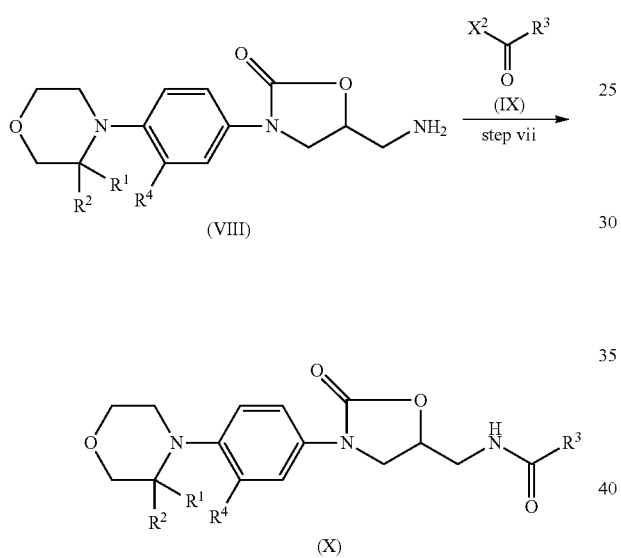

Step ii: converting the sulfate moiety of the compound having the formula (III) into a hydroxy group in the presence of water to provide a compound having the formula (IV)

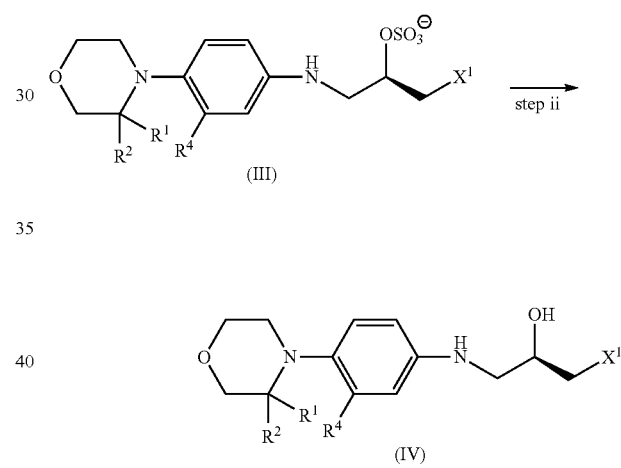

wherein $X^1$ is a leaving group;

$X^2$ is a leaving group which can be the same or different than $X^1$;

the moiety $C(R^1)(R^2)$ is C=O or $CH_2$;

$R^3$ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S, wherein the alkyl group, the aryl group and the heterocyclic group can be optionally substituted; and $R^4$ is H or halogen.

4. The method according to claim 3, wherein the method employs an enantiomerically enriched or enantiomerically pure starting material and which method comprises the steps of:

Step i: reacting a compound having the formula (I) with a compound having the formula (II) to provide a compound having the formula (III)

Step viii: cyclizing the compound having the formula (IV) to provide a compound having the formula (XI)

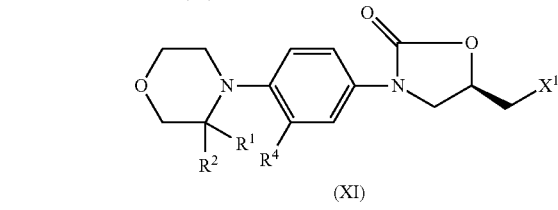

Step ix: optionally replacing the leaving group $X^1$ by a different leaving group $X^1$

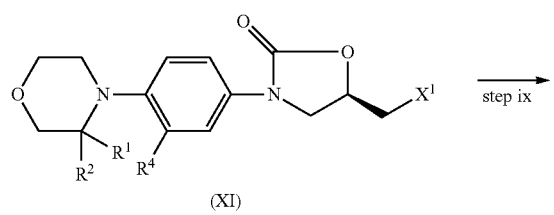

(XI)

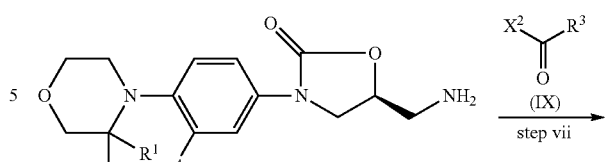

(VIII)

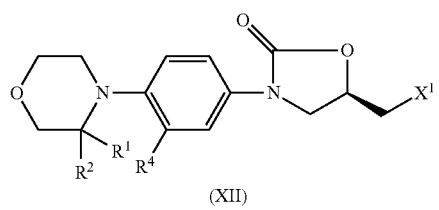

(XII)

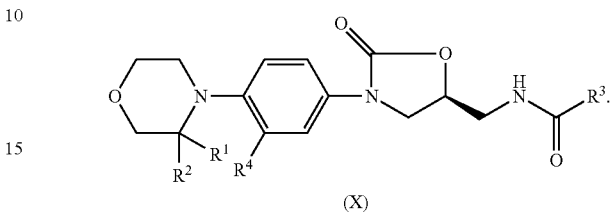

(X)

Step x: reacting the compound having the formula (XI) or (XII) with hexamethylenetetramine to provide a compound having the formula (XIII)

5. A method for the preparation of a compound having the formula (X), wherein the method comprises the steps of:

Step i: reacting a compound having the formula (I) with a compound having the formula (II) to provide a compound having the formula (III)

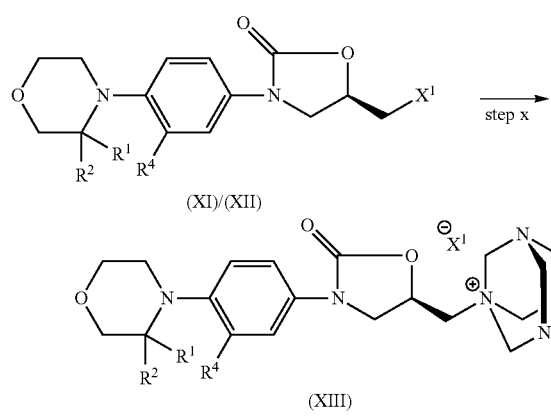

(XI)/(XII)

(XIII)

Step xi: removing the hexamethylenetetramine moiety of the compound having the formula (XIII) to provide a compound having the formula (VIII)

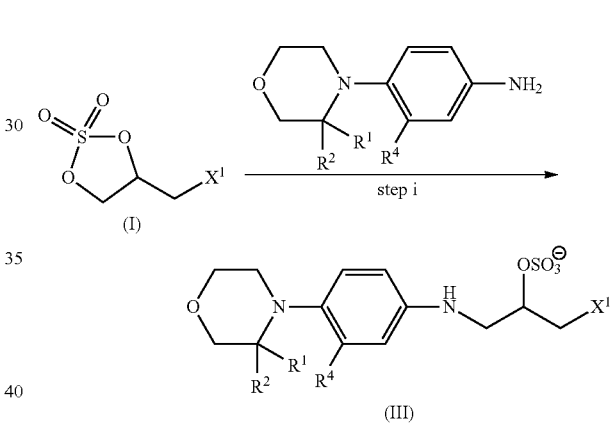

(I)

(III)

Step ii: converting the sulfate moiety of the compound having the formula (III) into a hydroxy group in the presence of water to provide a compound having the formula (IV)

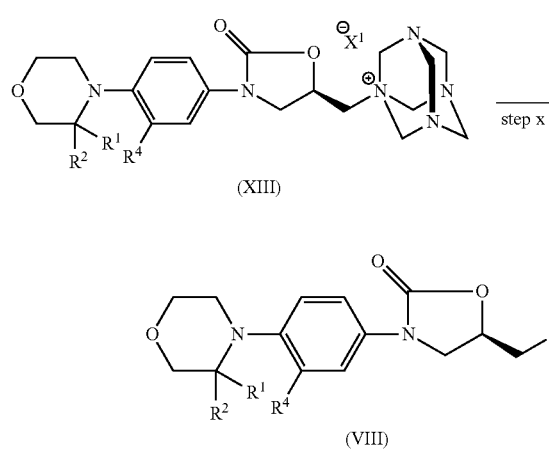

(XIII)

(VIII)

Step vii: reacting the compound having the formula (VIII) with a compound having the formula (IX) to provide a compound having the formula (X)

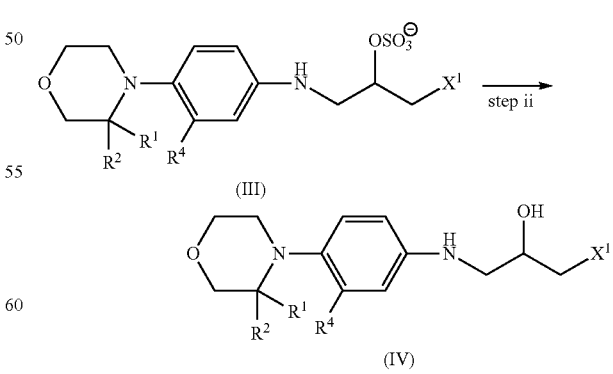

(III)

(IV)

Step iii: replacing the leaving group $X^1$ of the compound having the formula (IV) by $NH_3$ to provide a compound having the formula (V)

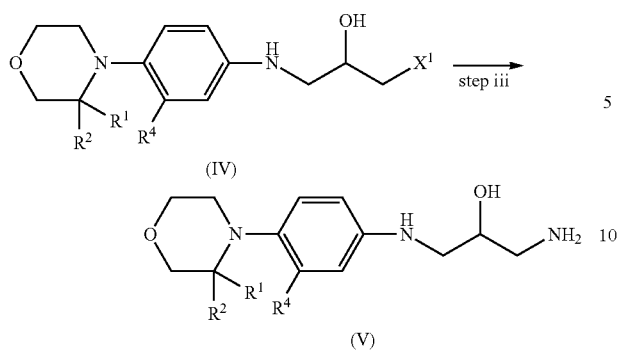

(IV)

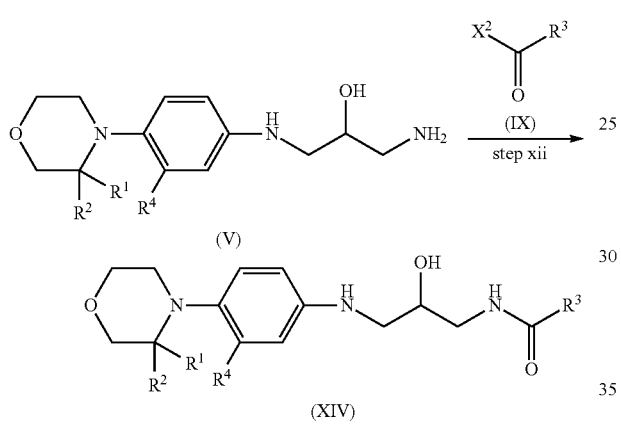

(V)

Step xii: reacting the compound having the formula (V) with a compound having the formula (IX) to provide a compound having the formula (XIV)

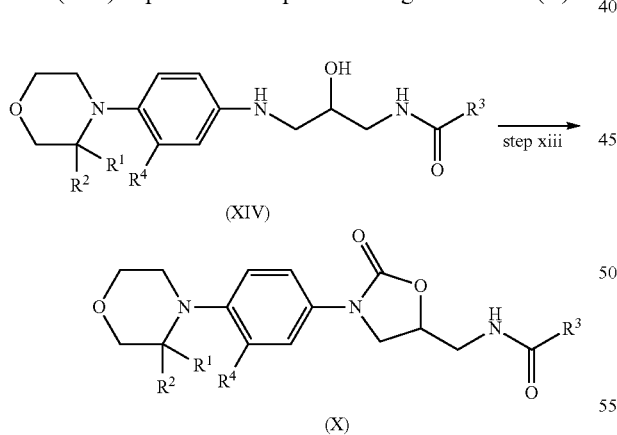

(XIV)

Step xiii: cyclizing the compound having the formula (XIV) to provide a compound having the formula (X)

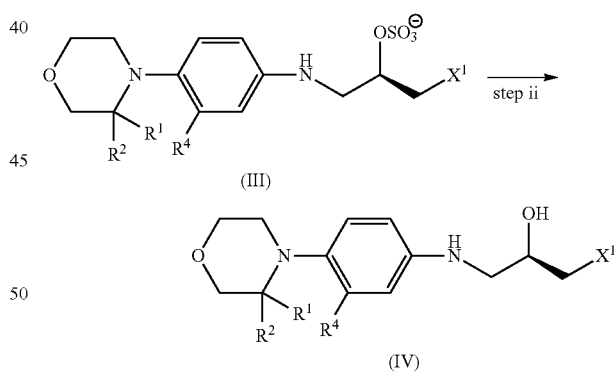

(XIV)

(X)

wherein $X^1$ is a leaving group;

$X^2$ is a leaving group which can be the same or different than $X^1$;

the moiety $C(R^1)(R^2)$ is C=O or $CH_2$;

$R^3$ is selected from the group consisting of an alkyl group having 1 to 6 carbon atoms, an aryl group having 6 to 10 carbon atoms and a heterocyclic group having 5 to 10 atoms which includes one or more heteroatoms selected from N, O and S, wherein the alkyl group, the aryl group and the heterocyclic group can be optionally substituted; and $R^4$ is H or halogen.

6. The method according to claim 5, wherein the method employs an enantiomerically enriched or enantiomerically pure starting material and which method comprises the steps of:

Step i: reacting a compound having the formula (I) with a compound having the formula (II) to provide a compound having the formula (III)

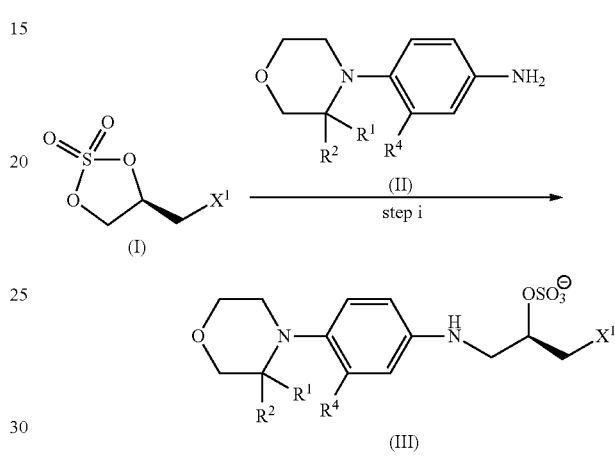

(III)

Step ii: converting the sulfate moiety of the compound having the formula (III) into a hydroxy group in the presence of water to provide a compound having the formula (IV)

(III)

(IV)

Step iii: replacing the leaving group $X^1$ of the compound having the formula (IV) by $NH_3$ to provide a compound having the formula (V)

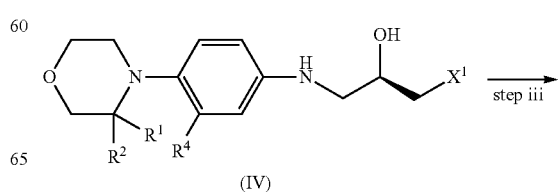

(IV)

-continued

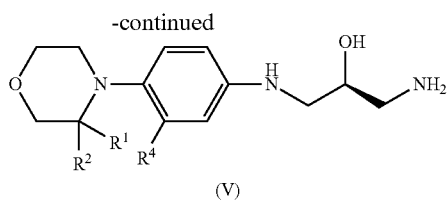

(V)

Step xii: reacting the compound having the formula (V) with a compound having the formula (IX) to provide a compound having the formula (XIV)

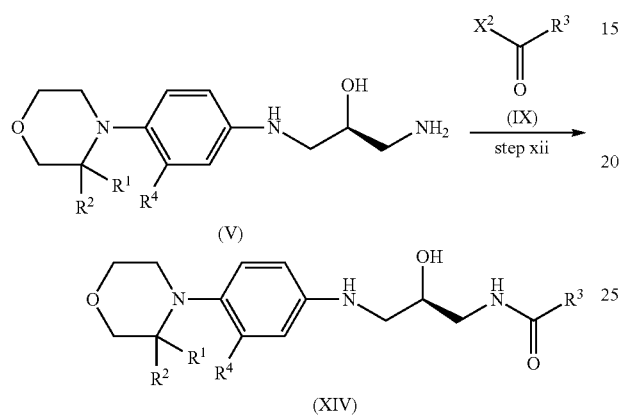

Step xiii: cyclizing the compound having the formula (XIV) to provide a compound having the formula (X)

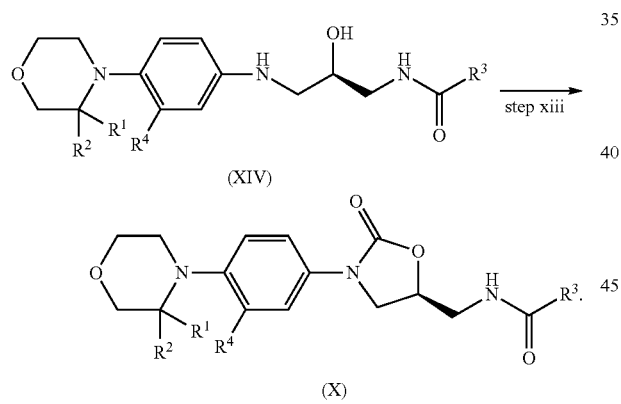

7. The method according to claim 1, wherein $CR^1R^2$ is C=O, $R^4$ is H and $R^3$ is

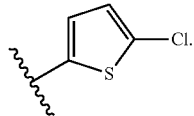 [SMILES: *c1ccc(Cl)s1]

8. The method according to claim 1, wherein $CR^1R^2$ is $CH_2$, $R^4$ is F and $R^3$ is $CH_3$.

9. The method according to claim 3, wherein step ix is conducted and the leaving group $X^1$ in the compound having the formula (XI) is Cl and the leaving group $X^1$ in the compound having the formula (XII) is I.

10. The method according to claim 3, wherein $CR'R^2$ is C=O, $R^4$ is H and $R^3$ is

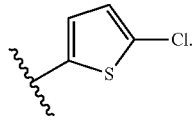 [SMILES: *c1ccc(Cl)s1]

11. The method according to claim 5, wherein $CR^1R^2$ is $CO_2$=O $R^4$ is H and $R^3$ is

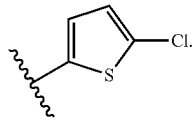 [SMILES: *c1ccc(Cl)s1]

12. The method according to claim 3, wherein $CR^1R^2$ is $CH_2$, $R^4$ is F and $R^3$ is $CH_3$.

13. The method according to claim 5, wherein $CR^1R^2$ is $CH_2$, $R^4$ is F and $R^3$ is $CH_3$.

* * * * *